United States Patent
Belson et al.

(10) Patent No.: US 6,610,007 B2
(45) Date of Patent: Aug. 26, 2003

(54) STEERABLE SEGMENTED ENDOSCOPE AND METHOD OF INSERTION

(75) Inventors: Amir Belson, Cupertino, CA (US); Paul DeWitt Frey, Redwood City, CA (US); Christine Wei Hsien Mcelhaney, San Carlos, CA (US); James Craig Milroy, Palo Alto, CA (US); Robert Matthew Ohline, Redwood City, CA (US); Joseph M. Tartaglia, Morgan Hill, CA (US)

(73) Assignee: Neoguide Systems, Inc., Campbell, CA (US)

(*) Notice: Subject to any disclaimer, the term of this patent is extended or adjusted under 35 U.S.C. 154(b) by 102 days.

(21) Appl. No.: 09/969,927

(22) Filed: Oct. 2, 2001

(65) Prior Publication Data

US 2002/0062062 A1 May 23, 2002

Related U.S. Application Data

(63) Continuation-in-part of application No. 09/790,204, filed on Feb. 20, 2001.
(60) Provisional application No. 60/194,140, filed on Apr. 3, 2000.

(51) Int. Cl.$^7$ .................................................. A61B 1/00
(52) U.S. Cl. .................... 600/146; 600/144; 604/95.01; 901/1
(58) Field of Search ................................. 600/145, 146, 600/117, 150, 151, 152, 143, 144; 604/95.01; 901/1

(56) References Cited

U.S. PATENT DOCUMENTS 3,610,231 A  10/1971  Takahashi et al.
3,739,770 A  6/1973  Mori (List continued on next page.)

FOREIGN PATENT DOCUMENTS

DE  37 07 787    9/1988
JP  63 136014    6/1988
JP  111458 A    5/1993
JP  5-1999 A    10/1993

OTHER PUBLICATIONS

Slatkin et al. (Aug. 1995). "The Development of a Robotic Endoscope," Proceedings 1995 IEEE/RSJ International Conference on Human Robot Interaction and Cooperative Robots. Pittsburgh, PA Aug. 5–9, 1995, Proceeding of the IEEE/RSJ International Conference on Intelligent Robot Syst. 2:162–171.

Lee, T.S. et al. (1994). "A Highly Redundant Robot System For Inspection," Proceedings of Conference on Intelligent Robots in Factory, Fields, Space and Service. Houston, TX Mar. 21–24, 1994 Part vol. 1:142–148

*Primary Examiner*—Linda C. M. Dvorak
*Assistant Examiner*—Jocelyn Ram
(74) *Attorney, Agent, or Firm*—Morrison & Foerster LLP

(57) ABSTRACT

A steerable endoscope has an elongated body with a selectively steerable distal portion and an automatically controlled proximal portion. The endoscope body is inserted into a patient and the selectively steerable distal portion is used to select a desired path within the patient's body. When the endoscope body is advanced, an electronic motion controller operates the automatically controlled proximal portion to assume the selected curve of the selectively steerable distal portion. Another desired path is selected with the selectively steerable distal portion and the endoscope body is advanced again. As the endoscope body is further advanced, the selected curves propagate proximally along the endoscope body, and when the endoscope body is withdrawn proximally, the selected curves propagate distally along the endoscope body. This creates a serpentine motion in the endoscope body allowing it to negotiate tortuous curves along a desired path through or around and between organs within the body.

48 Claims, 13 Drawing Sheets

U.S. PATENT DOCUMENTS

| | | |
|---|---|---|
| 3,773,034 A | 11/1973 | Burns et al. |
| 3,897,775 A | 8/1975 | Furihata |
| 3,946,727 A | 3/1976 | Okada et al. |
| 4,054,128 A | 10/1977 | Seufert et al. |
| 4,176,662 A | 12/1979 | Frazer |
| 4,236,509 A | 12/1980 | Takahashi et al. |
| 4,273,111 A | 6/1981 | Tsukaya |
| 4,327,711 A | 5/1982 | Takagi |
| 4,499,895 A | 2/1985 | Takayama |
| 4,503,842 A | 3/1985 | Takayama |
| 4,543,090 A | 9/1985 | McCoy |
| 4,559,928 A | 12/1985 | Takayama |
| 4,621,618 A | 11/1986 | Omagari |
| 4,753,223 A | 6/1988 | Bremer |
| 4,788,967 A | 12/1988 | Ueda |
| 4,799,474 A | 1/1989 | Ueda |
| 4,815,450 A | 3/1989 | Patel |
| 4,832,473 A | 5/1989 | Ueda |
| 4,873,965 A * | 10/1989 | Danieli ............ 600/141 |
| 4,879,991 A | 11/1989 | Ogiu |
| 4,884,557 A | 12/1989 | Takehana et al. |
| 4,895,431 A | 1/1990 | Tsujiuchi et al. |
| 4,899,731 A | 2/1990 | Takayama et al. |
| 4,904,048 A | 2/1990 | Sogawa et al. |
| 4,930,494 A * | 6/1990 | Takehana et al. ........ 600/145 |
| 4,971,035 A | 11/1990 | Ito |
| 4,987,314 A | 1/1991 | Gotanda et al. |
| 5,018,509 A | 5/1991 | Suzuki et al. |
| 5,125,395 A | 6/1992 | Adair |
| 5,159,446 A | 10/1992 | Hibino et al. |
| 5,243,967 A | 9/1993 | Hibino |
| 5,271,381 A | 12/1993 | Ailinger et al. |
| 5,337,732 A | 8/1994 | Grundfest et al. |
| 5,370,108 A | 12/1994 | Miura et al. |
| 5,383,852 A | 1/1995 | Stevens-Wright |
| 5,394,864 A | 3/1995 | Kobayashi et al. |
| 5,400,769 A | 3/1995 | Tanii et al. |
| 5,460,166 A | 10/1995 | Yabe et al. |
| 5,460,168 A | 10/1995 | Masubuchi et al. |
| 5,469,840 A | 11/1995 | Tanii et al. |
| 5,482,029 A | 1/1996 | Sekiguchi et al. |
| 5,487,757 A | 1/1996 | Truckai et al. |
| 5,507,717 A | 4/1996 | Kura et al. |
| 5,531,664 A | 7/1996 | Adachi et al. |
| 5,551,945 A | 9/1996 | Yabe et al. |
| 5,558,619 A | 9/1996 | Kami et al. |
| 5,577,992 A | 11/1996 | Chiba et al. |
| 5,624,380 A | 4/1997 | Takayama et al. |
| 5,626,553 A | 5/1997 | Frassica et al. |
| 5,645,520 A | 7/1997 | Nakamura et al. |
| 5,658,238 A | 8/1997 | Suzuki et al. |
| 5,662,587 A | 9/1997 | Grundfest et al. |
| 5,665,050 A | 9/1997 | Benecke |
| 5,667,476 A | 9/1997 | Frassica et al. |
| 5,733,245 A | 3/1998 | Kawano |
| 5,749,828 A * | 5/1998 | Solomon et al. ............ 600/141 |
| 5,752,912 A | 5/1998 | Takahashi et al. |
| 5,810,715 A | 9/1998 | Moriyama |
| 5,810,716 A * | 9/1998 | Mukherjee et al. ......... 600/146 |
| 5,860,914 A | 1/1999 | Chiba et al. |
| 5,876,373 A | 3/1999 | Giba et al. |
| 5,885,208 A | 3/1999 | Moriyama |
| 5,897,488 A | 4/1999 | Ueda |
| 5,906,591 A | 5/1999 | Dario et al. |
| 5,916,147 A | 6/1999 | Boury |
| 5,921,915 A | 7/1999 | Aznoian et al. |
| 5,976,074 A | 11/1999 | Moriyama |
| 5,989,182 A | 11/1999 | Hori et al. |
| 5,993,381 A | 11/1999 | Ito |
| 6,036,636 A | 3/2000 | Motoki et al. |
| 6,066,132 A | 5/2000 | Chen et al. |
| 6,162,171 A * | 12/2000 | Ng et al. .................... 600/141 |
| 6,402,687 B1 | 6/2002 | Ouchi |

* cited by examiner

STEERABLE SEGMENTED ENDOSCOPE AND METHOD OF INSERTION

CROSS-REFERENCE TO OTHER APPLICATIONS

The present application is a continuation-in-part of U.S. patent application Ser. No. 09/790,204 entitled "Steerable Endoscope and Improved Method of Insertion" filed Feb. 20, 2001, which claims priority of U.S. Provisional Patent Application No. 60/194,140 filed Apr. 3, 2000.

FIELD OF THE INVENTION

The present invention relates generally to endoscopes and endoscopic medical procedures. More particularly, it relates to a method and apparatus to facilitate insertion of a flexible endoscope along a tortuous path, such as for colonoscopic examination and treatment.

BACKGROUND OF THE INVENTION

An endoscope is a medical instrument for visualizing the interior of a patient's body. Endoscopes can be used for a variety of different diagnostic and interventional procedures, including colonoscopy, bronchoscopy, thoracoscopy, laparoscopy and video endoscopy.

Colonoscopy is a medical procedure in which a flexible endoscope, or colonoscope, is inserted into a patient's colon for diagnostic examination and/or surgical treatment of the colon. A standard colonoscope is typically 135–185 cm in length and 12–19 mm in diameter, and includes a fiberoptic imaging bundle or a miniature camera located at the instrument's tip, illumination fibers, one or two instrument channels that may also be used for insufflation or irrigation, air and water channels, and vacuum channels. The colonoscope is inserted via the patient's anus and is advanced through the colon, allowing direct visual examination of the colon, the ileocecal valve and portions of the terminal ileum. Insertion of the colonoscope is complicated by the fact that the colon represents a tortuous and convoluted path. Considerable manipulation of the colonoscope is often necessary to advance the colonoscope through the colon, making the procedure more difficult and time consuming and adding to the potential for complications, such as intestinal perforation. Steerable colonoscopes have been devised to facilitate selection of the correct path though the curves of the colon. However, as the colonoscope is inserted farther and farther into the colon, it becomes more difficult to advance the colonoscope along the selected path. At each turn, the wall of the colon must maintain the curve in the colonoscope. The colonoscope rubs against the mucosal surface of the colon along the outside of each turn. Friction and slack in the colonoscope build up at each turn, making it more and more difficult to advance and withdraw the colonoscope. In addition, the force against the wall of the colon increases with the buildup of friction. In cases of extreme tortuosity, it may become impossible to advance the colonoscope all of the way through the colon.

Steerable endoscopes, catheters and insertion devices for medical examination or treatment of internal body structures are described in the following U.S. patents, the disclosures of which are hereby incorporated by reference in their entirety: U.S. Pat. Nos. 4,753,223; 5,337,732; 5,662,587; 4,543,090; 5,383,852; 5,487,757 and 5,337,733.

SUMMARY OF THE INVENTION

In keeping with the foregoing discussion, the present invention takes the form of a steerable endoscope for negotiating tortuous paths through a patient's body. The steerable endoscope can be used for a variety of different diagnostic and interventional procedures, including colonoscopy, upper endoscopy, bronchoscopy, thoracoscopy, laparoscopy and video endoscopy. The steerable endoscope is particularly well suited for negotiating the tortuous curves encountered when performing a colonoscopy procedure.

The steerable endoscope has an elongated body with a manually or selectively steerable distal portion and an automatically controlled proximal portion. The selectively steerable distal portion can be selectively steered or bent up to a full 180 degree bend in any direction. A fiberoptic imaging bundle and one or more illumination fibers extend through the body from the proximal end to the distal end. Alternatively, the endoscope can be configured as a video endoscope with a miniaturized video camera, such as a CCD camera, which transmits images to a video monitor by a transmission cable or by wireless transmission, or alternatively through the use of CMOS imaging technology. Optionally, the endoscope may include one or two instrument channels that may also be used for insufflation or irrigation, air and water channels, and vacuum channels.

A proximal handle attached to the elongate body includes an ocular for direct viewing and/or for connection to a video camera, a connection to an illumination source and one or more luer lock fittings that are connected to the instrument channels. The handle is connected to a steering control for selectively steering or bending the selectively steerable distal portion in the desired direction and to an electronic motion controller for controlling the automatically controlled proximal portion of the endoscope. An axial motion transducer is provided to measure the axial motion of the endoscope body as it is advanced and withdrawn. Optionally, the endoscope may include a motor or linear actuator for both automatically advancing and withdrawing the endoscope, or for automatically advancing and passively withdrawing the endoscope.

One preferable embodiment of the endoscope includes a segmented endoscopic embodiment having multiple independently controllable segments which may be individually motorized and interconnected by joints. Each of the individual adjacent segments may be pivotable about two independent axes to offer a range of motion during endoscope insertion into a patient.

This particular embodiment, as mentioned, may have individual motors, e.g., small brushed DC motors, to actuate each individual segment. Furthermore, each segment preferably has a backbone segment which defines a lumen therethrough to allow a continuous lumen to pass through the entire endoscopic instrument to provide an access channel through which wires, optical fibers, air and/or water channels, various endoscopic tools, or any variety of devices and wires may be routed. The entire assembly, i.e., motors, backbone, cables, etc., may be encased or covered in a biocompatible material, e.g., a polymer, which is also preferably lubricious to allow for minimal frictional resistance during endoscope insertion and advancement into a patient. This biocompatible cover may be removable from the endoscopic body to expose the motors and backbone assembly to allow for direct access to the components. This may also allow for the cover to be easily replaced and disposed after use in a patient.

The method of the present invention involves inserting the distal end of the endoscope body into a patient, either through a natural orifice or through an incision, and steering the selectively steerable distal portion to select a desired path. When the endoscope body is advanced or inserted further into the patient's body, the electronic motion controller operates the automatically controlled proximal portion of the body to assume the selected curve of the selectively steerable distal portion. This process is repeated by selecting another desired path with the selectively steerable distal portion and advancing the endoscope body again. As the endoscope body is further advanced, the selected curves propagate proximally along the endoscope body. Similarly, when the endoscope body is withdrawn proximally, the selected curves propagate distally along the endoscope body, either automatically or passively. This creates a sort of serpentine motion in the endoscope body that allows it to negotiate tortuous curves along a desired path through or around and between organs within the body.

The method can be used for performing colonoscopy or other endoscopic procedures, such as bronchoscopy, thoracoscopy, laparoscopy and video endoscopy. In addition, the apparatus and methods of the present invention can be used for inserting other types of instruments, such as surgical instruments, catheters or introducers, along a desired path within the body.

DETAILED DESCRIPTION OF THE INVENTION

Figure 1:
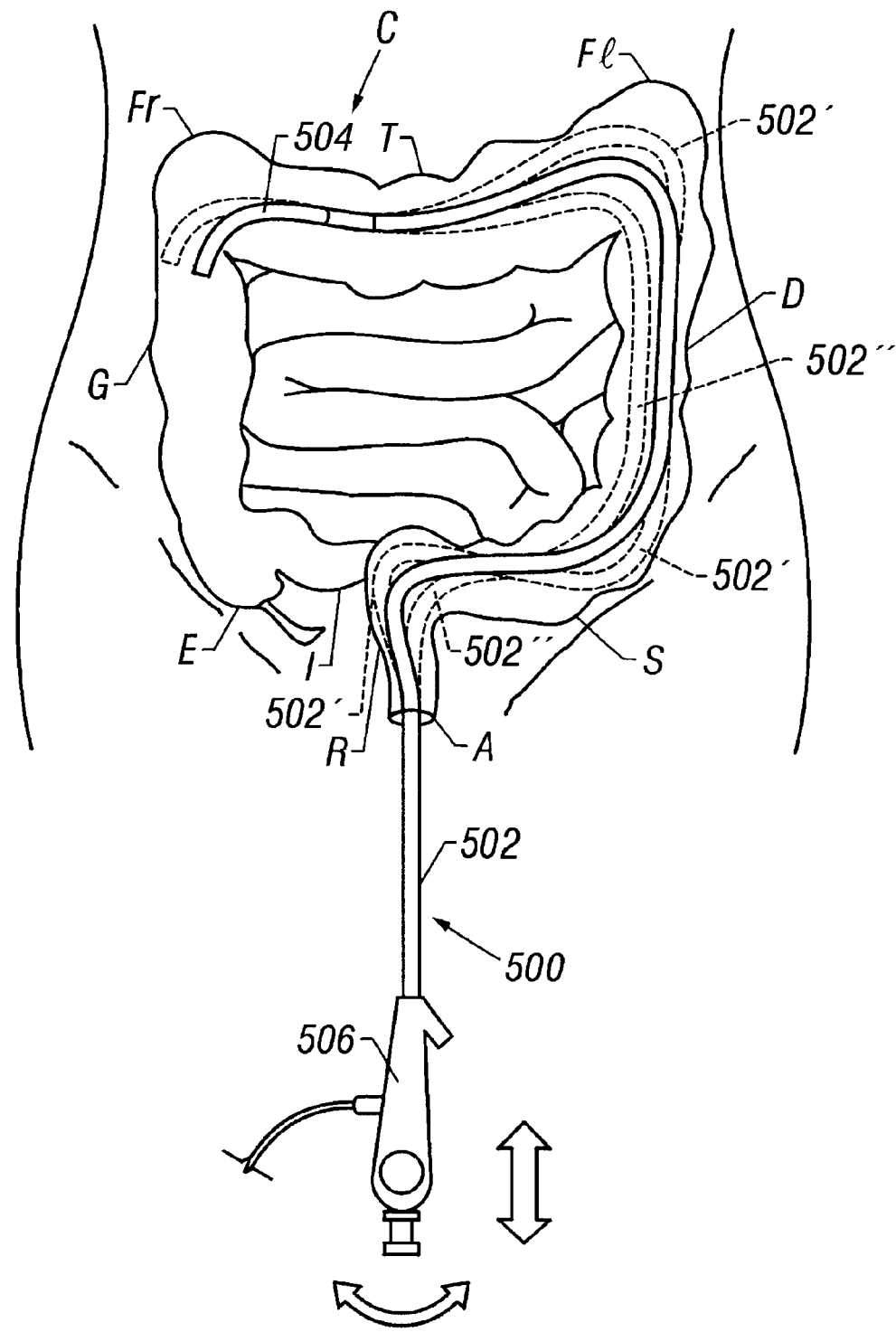
FIG. 1 shows a prior art colonoscope being employed for a colonoscopic examination of a patient's colon.

FIG. 1 shows a prior art colonoscope 500 being employed for a colonoscopic examination of a patient's colon C. The colonoscope 500 has a proximal handle 506 and an elongate body 502 with a steerable distal portion 504. The body 502 of the colonoscope 500 has been lubricated and inserted into the colon C via the patient's anus A. Utilizing the steerable distal portion 504 for guidance, the body 502 of the colonoscope 500 has been maneuvered through several turns in the patient's colon C to the ascending colon G. Typically, this involves a considerable amount of manipulation by pushing, pulling and rotating the colonoscope 500 from the proximal end to advance it through the turns of the colon C. After the steerable distal portion 504 has passed, the wall of the colon C maintains the curve in the flexible body 502 of the colonoscope 500 as it is advanced. Friction develops along the body 502 of the colonoscope 500 as it is inserted, particularly at each turn in the colon C. Because of the friction, when the user attempts to advance the colonoscope 500, the body 502' tends to move outward at each curve, pushing against the wall of the colon C, which exacerbates the problem by increasing the friction and making it more difficult to advance the colonoscope 500. On the other hand, when the colonoscope 500 is withdrawn, the body 502" tends to move inward at each curve taking up the slack that developed when the colonoscope 500 was advanced. When the patient's colon C is extremely tortuous, the distal end of the body 502 becomes unresponsive to the user's manipulations, and eventually it may become impossible to advance the colonoscope 500 any farther. In addition to the difficulty that it presents to the user, tortuosity of the patient's colon also increases the risk of complications, such as intestinal perforation.

Figure 2:
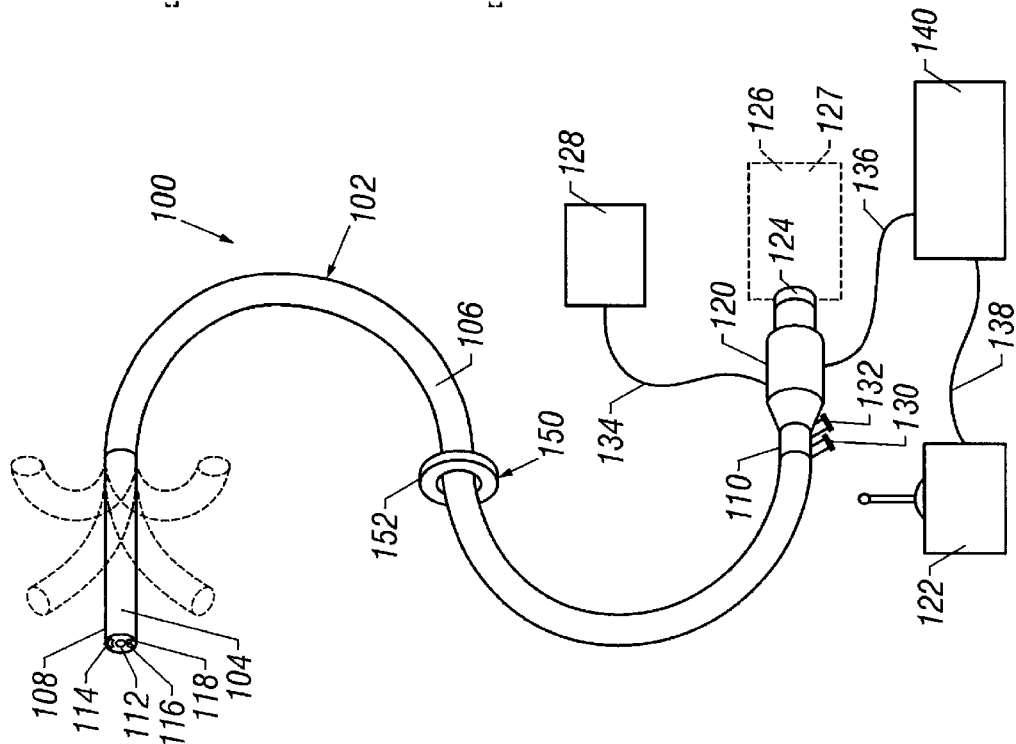
FIG. 2 shows a first embodiment of the steerable endoscope of the present invention.

FIG. 2 shows a first embodiment of the steerable endoscope 100 of the present invention. The endoscope 100 has an elongate body 102 with a manually or selectively steerable distal portion 104 and an automatically controlled proximal portion 106. The selectively steerable distal portion 104 can be selectively steered or bent up to a full 180 degree bend in any direction. A fiberoptic imaging bundle 112 and one or more illumination fibers 114 extend through the body 102 from the proximal end 110 to the distal end 108. Alternatively, the endoscope 100 can be configured as a video endoscope with a miniaturized video camera, such as a CCD camera, positioned at the distal end 108 of the endoscope body 102. The images from the video camera can be transmitted to a video monitor by a transmission cable or by wireless transmission where images may be viewed in real-time or recorded by a recording device onto analog recording medium, e.g., magnetic tape, or digital recording medium, e.g., compact disc, digital tape, etc. Optionally, the body 102 of the endoscope 100 may include one or two instrument channels 116, 118 that may also be used for insufflation or irrigation, air and water channels, and vacuum channels. The body 102 of the endoscope 100 is highly flexible so that it is able to bend around small diameter curves without buckling or kinking while maintaining the various channels intact. When configured for use as a colonoscope, the body 102 of the endoscope 100 is typically from 135 to 185 cm in length and approximately 12–13 mm in diameter. The endoscope 100 can be made in a variety of other sizes and configurations for other medical and industrial applications.

A proximal handle 120 is attached to the proximal end 110 of the elongate body 102. The handle 120 includes an ocular 124 connected to the fiberoptic imaging bundle 112 for direct viewing and/or for connection to a video camera 126 or a recording device 127. The handle 120 is connected to an illumination source 128 by an illumination cable 134 that is connected to or continuous with the illumination fibers 114. A first luer lock fitting, 130 and a second luer lock fitting 132 on the handle 120 are connected to the instrument channels 116, 118.

The handle 120 is connected to an electronic motion controller 140 by way of a controller cable 136. A steering control 122 is connected to the electronic motion controller 140 by way of a second cable 13 M. The steering control 122 allows the user to selectively steer or bend the selectively steerable distal portion 104 of the body 102 in the desired direction. The steering control 122 may be a joystick controller as shown, or other known steering control mechanism. The electronic motion controller 140 controls the motion of the automatically controlled proximal portion 106 of the body 102. The electronic motion controller 140 may be implemented using a motion control program running on a microcomputer or using an application-specific motion controller. Alternatively, the electronic motion controller 140 may be implemented using, a neural network controller.

An axial motion transducer 150 is provided to measure the axial motion of the endoscope body 102 as it is advanced and withdrawn. The axial motion transducer 150 can be made in many possible configurations. By way of example, the axial motion transducer 150 in FIG. 2 is configured as a ring 152 that surrounds the body 102 of the endoscope 100. The axial motion transducer 150 is attached to a fixed point of reference, such as the surgical table or the insertion point for the endoscope 100 on the patient's body. As the body 102 of the endoscope 100 slides through the axial motion transducer 150, it produces a signal indicative of the axial position of the endoscope body 102 with respect to the fixed point of reference and sends a signal to the electronic motion controller 140 by telemetry or by a cable (not shown). The axial motion transducer 150 may use optical, electronic or mechanical means to measure the axial position of the endoscope body 102. Other possible configurations for the axial motion transducer 150 are described below.

Figure 3:
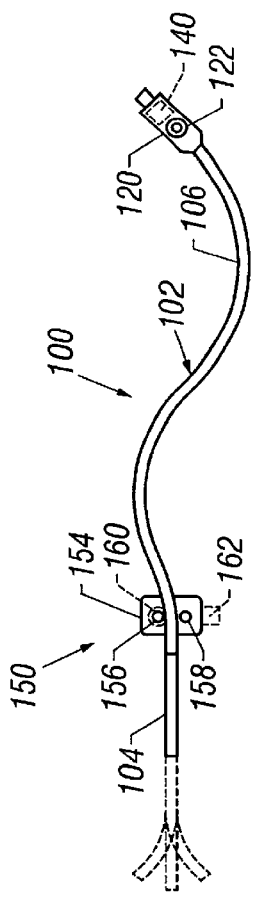
FIG. 3 shows a second embodiment of the steerable endoscope of the present invention.

FIG. 3 shows a second embodiment of the endoscope 100 of the present invention. As in the embodiment of FIG. 2, the endoscope 100 has an elongate body 102 with a selectively steerable distal portion 104 and an automatically controlled proximal portion 106. The steering control 122 is integrated into proximal handle 120 in the form or one or two dials for selectively steering, the selectively steerable distal portion 104 of the endoscope 100. Optionally, the electronic motion controller 140 may be miniaturized and integrated into proximal handle 120, as well. In this embodiment, the axial motion transducer 150 is configured with a base 154 that is attachable to a fixed point of reference, such as the surgical table. A first roller 156 and a second roller 158 contact the exterior of the endoscope body 102. A multi-turn potentiometer 160 or other motion transducer is connected to the first roller 156 to measure the axial motion of the endoscope body 102 and to produce a signal indicative of the axial position.

The endoscope 100 may be manually advanced or withdrawn by the user by grasping the body 102 distal to the axial motion transducer 150. Alternatively, the first roller 156 and/or second roller 158 may be connected to at least one motor, e.g., motor 162, for automatically advancing and withdrawing the body 102 of the endoscope 100.

Figure 4:
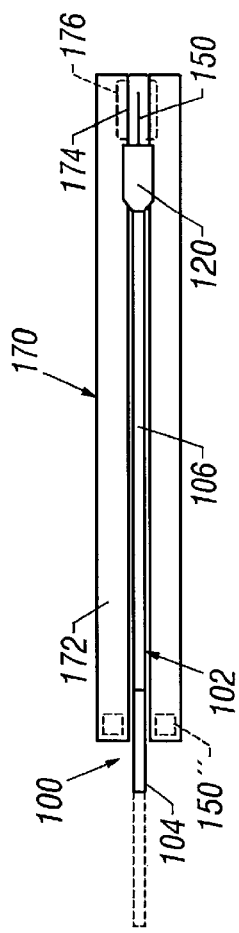
FIG. 4 shows a third embodiment of the steerable endoscope of the present invention.

FIG. 4 shows a third embodiment of the endoscope 100 of the present invention, which utilizes an elongated housing 170 to organize and contain the endoscope 100. The housing 170 has a base 172 with a linear track 174 to guide the body 102 of the endoscope 100. The housing 170 may have an axial motion transducer 150' that is configured as a linear motion transducer integrated into the linear track 174. Alternatively, the housing, 170 may have an axial motion transducer 150" configured similarly to the axial motion transducer 150 in FIG. 2 or 3. The endoscope 100 may be manually advanced or withdrawn by the user by grasping the body 102 distal to the housing 170. Alternatively, the housing 170 may include a motor 176 or other linear motion actuator for automatically advancing and withdrawing the body 102 of the endoscope 100. In another alternative configuration, a motor with friction wheels, similar to that described above in connection with FIG. 3, may be integrated into the axial motion transducer 150".

Figure 5:
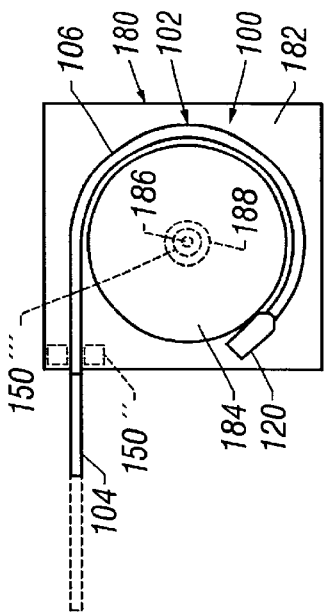
FIG. 5 shows a fourth embodiment of the steerable endoscope of the present invention.

FIG. 5 shows a fourth embodiment of the endoscope 100 of the present invention, which utilizes a rotary housing 180 to organize and contain the endoscope 100. The housing 180 has a base 182 with a rotating drum 184 to guide the body 102 of the endoscope 100. The housing 180 may have an axial motion transducer 150''' that is configured as a potentiometer connected to the pivot axis 186 of the rotating drum 184. Alternatively, the housing 180 may have an axial motion transducer 150" configured similarly to the axial motion transducer 150 in FIG. 2 or 3. The endoscope 100 may be manually advanced or withdrawn by the user by grasping the body 102 distal to the housing 180. Alternatively, the housing 180 may include a motor 188 connected to the rotating drum 184 for automatically advancing and withdrawing the body 102 of the endoscope 100. In another alternative configuration, a motor with friction wheels, similar to that described above in connection with FIG. 3, may be integrated into the axial motion transducer 150".

Figure 6:
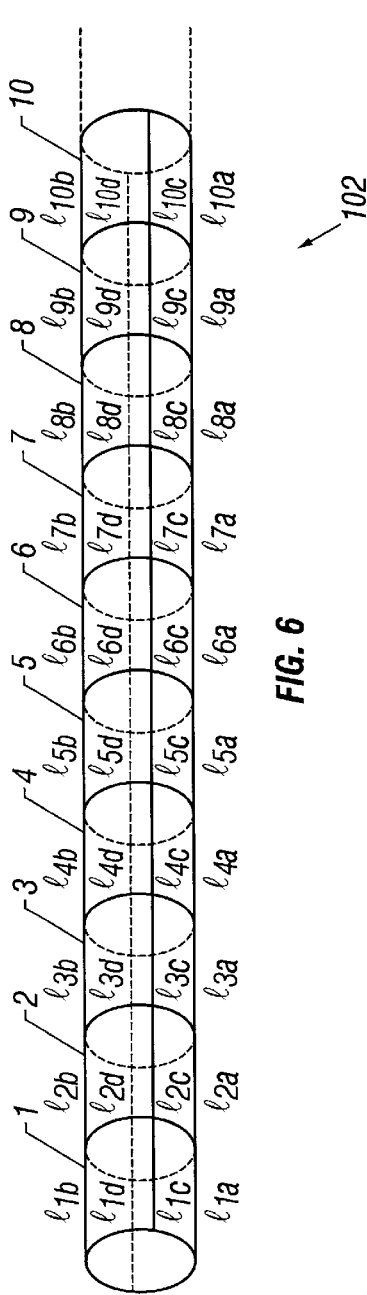
FIG. 6 shows a wire frame model of a section of the body of the endoscope in a neutral or straight position.

FIG. 6 shows a wire frame model of a section of the body 102 of the endoscope 100 in a neutral or straight position. Most of the internal structure of the endoscope body 102 has been eliminated in this drawing for the sake of clarity. The endoscope body 102 is divided up into sections 1, 2, 3 . . . 10, etc. The geometry of each section is defined by four length measurements along the a, b, c and d axes. For example, the geometry of section 1 is defined by the four length measurements $1_{1a}$, $1_{1b}$, $1_{1c}$, $1_{1d}$, and the geometry of section 2 is defined by the four length measurements $1_{2a}$, $1_{2b}$, $1_{2c}$, $1_{2d}$, etc. Preferably, each of the length measurements is individually controlled by a linear actuator (not shown). The linear actuators may utilize one of several different operating principles. For example, each of the linear actuators may be a self-heating NiTi alloy linear actuator or an electrorheological plastic actuator, or other known mechanical, pneumatic, hydraulic or electromechanical actuator. The geometry of each section may be altered using the linear actuators to change the four length measurements along the a, b, c and d axes. Preferably, the length measurements are changed in complementary pairs to selectively bend the endoscope body 102 in a desired direction. For example, to bend the endoscope body 102 in the direction of the a axis, the measurements $1_{1a}$, $1_{2a}$, $1_{3a}$, . . . $1_{10a}$ would be shortened and the measurements $1_{1b}$, $1_{2b}$, $1_{3b}$, . . . $1_{10b}$ would be lengthened an equal amount. The amount by which these measurements are changed determines the radius of the resultant curve.

In the selectively steerable distal portion 104 of the endoscope body 102, the linear actuators that control the a, b, c and d axis measurements of each section are selectively controlled by the user through the steering control 122. Thus, by appropriate control of the a, b, c and d axis measurements, the selectively steerable distal portion 104 of the endoscope body 102 can be selectively steered or bent up to a full 180 degrees in any direction.

Figure 7:
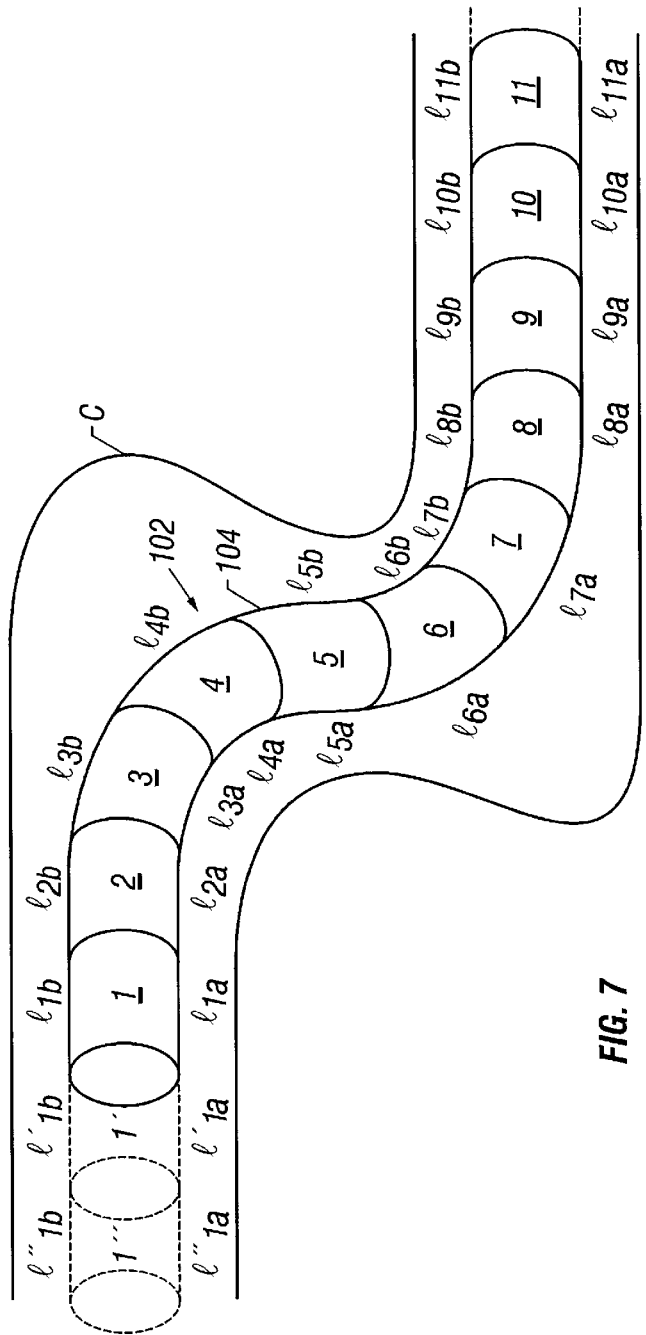
FIG. 7 shows the wire frame model of the endoscope body shown in FIG. 6 passing through a curve in a patient's colon.

In the automatically controlled proximal portion 106, however, the a, b, c and d direction measurements of each section are automatically controlled by the electronic motion controller 140, which uses a curve propagation method to control the shape of the endoscope body 102. To explain how the curve propagation method operates, FIG. 7 shows the wire frame model of a part of the automatically controlled proximal portion 106 of the endoscope body 102 shown in FIG. 6 passing, through a curve in a patient's colon C. For simplicity, an example of a two-dimensional curve is shown and only the a and b axes will be considered. In a three-dimensional curve all four of the a, b, c and d axes would be brought into play.

In FIG. 7, the endoscope body 102 has been maneuvered through the curve in the colon C with the benefit of the selectively steerable distal portion 104 (this part of the procedure is explained in more detail below) and now the automatically controlled proximal portion 106 resides in the curve. Sections 1 and 2 are in a relatively straight part of the colon C, therefore $l_{1a}=l_{1b}$ and $l_{2a}=l_{2b}$. However, because sections 3–7 are in the S-shaped curved section, $l_{3a}<l_{3b}$, $l_{4a}<l_{4d}$ and $l_{5a}<l_{5b}$, but $l_{6a}>l_{6b}$, $l_{7a}>l_{7b}$ and $l_{8a}>l_{8b}$. When the endoscope body 102 is advanced distally by one unit, section 1 moves into the position marked 1', section 2 moves into the position previously occupied by section 1, section 3 moves into the position previously occupied by section 2, etc. The axial motion transducer 150 produces a signal indicative of the axial position of the endoscope body 102 with respect to a fixed point of reference and sends the signal to the electronic motion controller 140, under control of the electronic motion controller 140, each time the endoscope body 102 advances one unit, each section in the automatically controlled proximal portion 106 is signaled to assume the shape of the section that previously occupied the space that it is now in. Therefore, when the endoscope body 102 is advanced to the position marked 1', $l_{1a}=l_{1b}$, $l_{2a}=l_{2b}$, $l_{3a}=l_{3b}$, $l_{4a}<l_{4b}$, $l_{5a}<l_{5b}$, $l_{6a}<l_{6b}$, $l_{7a}>l_{7b}$ and $l_{8a}>l_{8b}$, and $l_{9a}<l_b$, when the endoscope body 102 is advanced to the position marked 1", $l_{1a}=l_{1b}$, $l_{2a}=l_2$, $l_{3a}=l_{3b}$, $l_{4a}=l_{4b}$, $l_{5a}<l_{5b}$, $l_{6a}<l_{6b}$, $l_{7a}<l_{7b}$, $l_{8a}>l_{8b}$, $l_{9a}>l_{9b}$, and $l_{10a}>l_{10b}$. Thus, the S-shaped curve propagates proximally along the length of the automatically controlled proximal portion 106 of the endoscope body 102. The S-shaped curve appears to be fixed in space, as the endoscope body 102 advances distally.

Similarly, when the endoscope body 102 is withdrawn proximally, each time the endoscope body 102 is moved proximally by one unit, each section in the automatically controlled proximal portion 106 is signaled to assume the shape of the section that previously occupied the space that it is now in. The S-shaped curve propagates distally along the length of the automatically controlled proximal portion 106 of the endoscope body 102, and the S-shaped curve appears to be fixed in space, as the endoscope body 102 withdraws proximally.

Whenever the endoscope body 102 is advanced or withdrawn, the axial motion transducer 150 detects the change in position and the electronic motion controller 140 propagates the selected curves proximally or distally along the automatically controlled proximal portion 106 of the endoscope body 102 to maintain the curves in a spatially fixed position. This allows the endoscope body 102 to move through tortuous curves without putting unnecessary force on the wall of the colon C.

Figure 9:
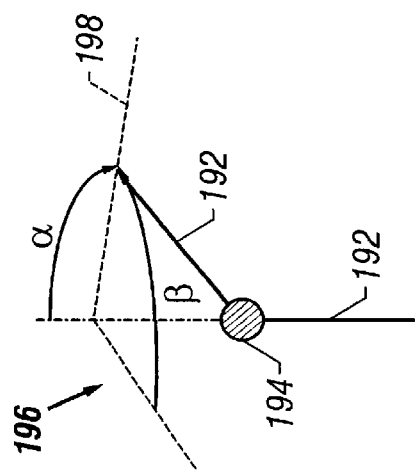
FIG. 9 shows a partial schematic representation of the embodiment of FIG. 8 showing two segments being pivotable about two independent axes.
Figure 8:
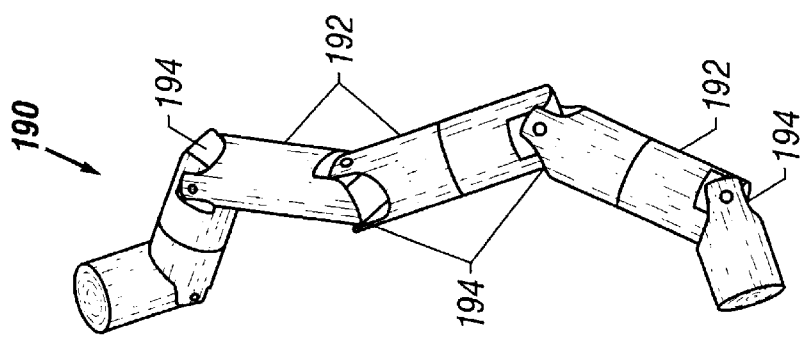
FIG. 8 shows a representative portion of an alternative endoscopic body embodiment having multiple segments interconnected by joints.

FIG. 8 shows a representative portion of an alternative endoscopic body embodiment 190 which has multiple segments 192 interconnected by joints 194. In this embodiment, adjacent segments 192 can be moved or angled relative to one another by a joint 194 having at least one degree-of-freedom, and preferably having multiple degrees-of-freedom, preferably about two axes as shown here. As seen further in FIG. 9, a partial schematic representation 196 of the embodiment 190 is shown where two segments 192 may be rotated about joint 194 about the two independent axes. The range of motion may be described in relation to spherical axes 198 by angles $\alpha$ and $\beta$.

Figure 10:
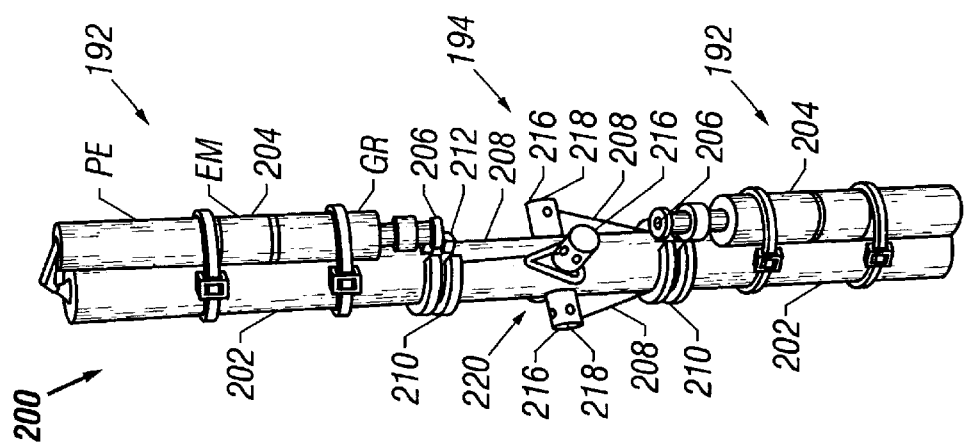
FIG. 10 shows a preferable endoscope embodiment having motorized segmented joints.

As mentioned above, such a segmented body may be actuated by a variety of methods. A preferable method involves the use of electromechanical motors individually mounted on each individual segment to move the segments relative to one another. FIG. 10 shows a preferable embodiment 200 having motorized segmented joints. Each segment 192 is preferably comprised of a backbone segment 202, which also preferably defines at least one lumen running through it to provide an access channel through which wires, optical fibers, air and/or water channels, various endoscopic tools, or any variety of devices and wires may be routed through. The backbone segment may be made of a variety of materials which are preferably biocompatible and which provide sufficient strength to support the various tools and other components, e.g., stainless steel. Although much of the description is to an individual segment 192, each of the segments 192 are preferably identical, except for the segment (or first few segments) located at the distal tip, and the following description readily applies to at least a majority of the segments 192.

A single motor, or multiple motors depending upon the desired result and application, may be attached to at least a majority of the segments. An embodiment having a single motor on a segment is illustrated in FIG. 10 where an individual motor 204 is preferably attached to backbone 202 and is sufficiently small and compact enough so as to present a relatively small diameter which is comfortable and small enough for insertion into a patient without trauma. Motor 204, which is shown here as being a small brushed DC motor, may be used for actuating adjacent segments 192 and may be controlled independently from other motors. Various motors, aside from small brushed DC motors, may also be used such as AC motors, linear motors, etc. Each motor 204 also preferably contains within the housing not only the electromechanical motor assembly EM itself, but also a gear reduction stage GR, and a position encoder PE. A gear reduction stage GR attached to the motor assembly EM will allow for the use of the motor 204 in its optimal speed and torque range by changing high-speed, low-torque operating conditions into a more useful low-speed, high-torque output. The position encoder PE may be a conventional encoder to allow the controlling computer to read the position of the segment's joint 194 by keeping track of the angular rotational movement of the output shaft of the motor 204.

Each motor 204 has a rotatable shaft which extends from an end of the motor 204 to provide for the transmission of power to actuate the segments 192. Upon this shaft, a spool 206 may be rotatingly attached with a first end of the cable 208 further wound about the spool 206. The cable 208 may then be routed from spool 206 through a channel 212 which is defined in the cable guide 210 and out through opening 214 (as seen in greater detail in FIGS. 11A–11B) to cable anchor 216, to which the second end of the cable 208 is preferably attached, e.g., by crimping and/or soldering. The cable guide 210 serves to capture the cable 208 that is wound about the spool 206. The cable anchor 216 is attached across a universal joint pivot 220 to an adjacent segment 192 via a pin 218 and may be shaped like a conventional electronic ring connector having a round section defining a hole therethrough for mounting to the segment 192 and an extension protruding from the anchor 216 for attaching the second end of the cable 208. Cable 208 may comprise a wide variety of filaments, strands, wires, chains, braids, etc. any of which may be made of a wide variety of biocompatible materials, e.g., metals such as stainless steel, polymers such as plastics and Nylon, etc.

In operation, when the motor 204 is operated to spin the shaft in a first direction, e.g., clockwise, the spool 206 rotates accordingly and the cable 208 pulls in a corresponding direction on the adjacent segment 192 and transmits the torque to subsequently actuate it along a first axis. When the motor 204 is operated to spin the shaft in a second direction opposite to the first, e.g., counter-clockwise, the spool 206 again rotates accordingly and the cable 208 would then pull in the corresponding opposing direction on the adjacent segment 192 to subsequently transmit the torque and actuate it in the opposite direction.

Figure 11A:
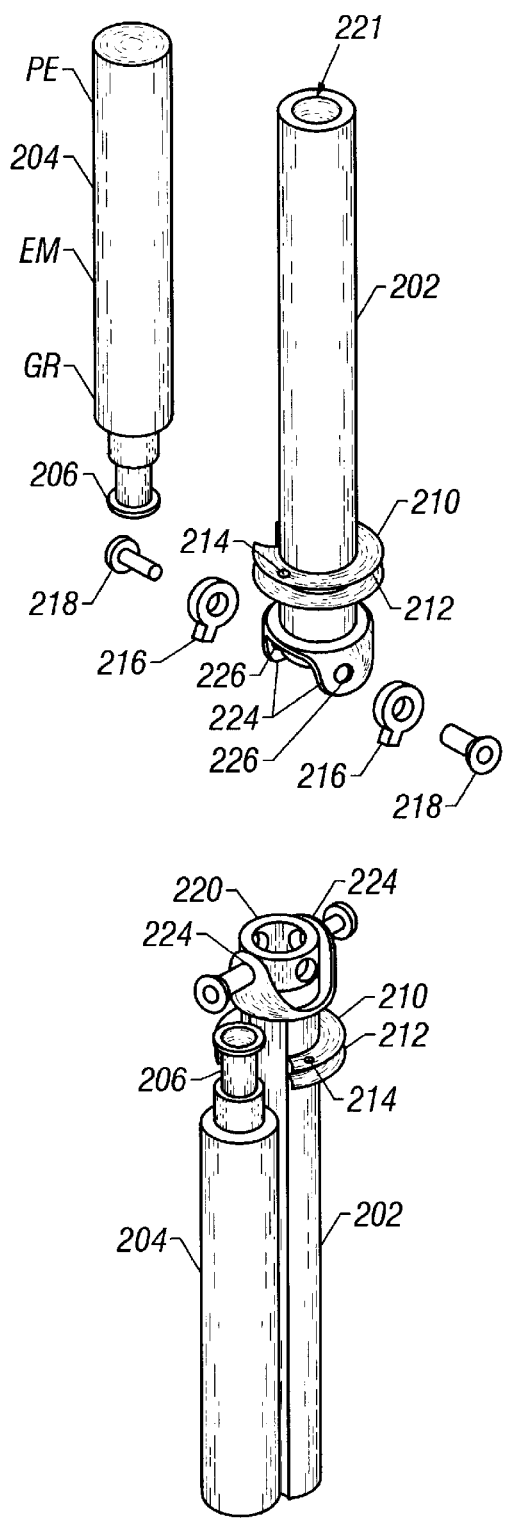
FIGS. 11A–11B show exploded isometric assembly views of two adjacent segments and an individual segment, respectively, from the embodiment shown in FIG. 10.
Figure 11B:
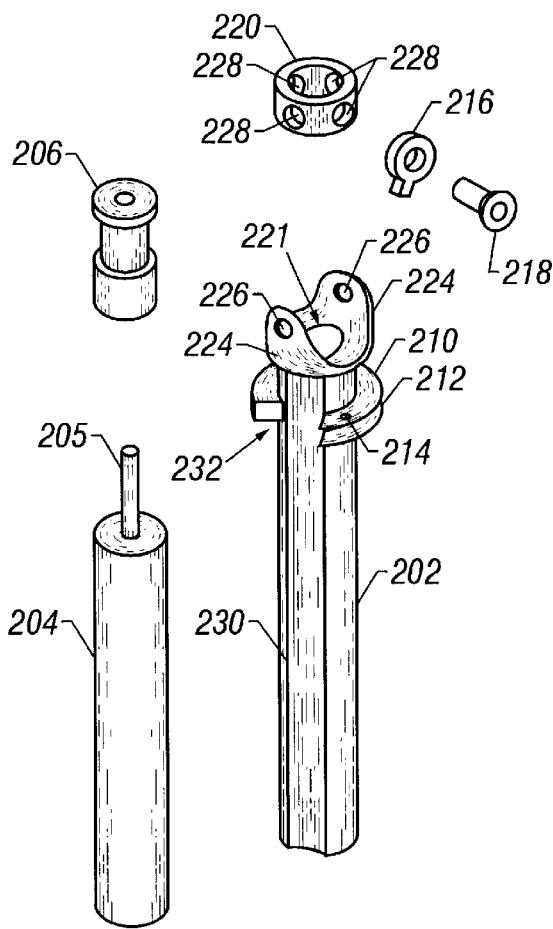

FIGS. 11A and 11B show exploded isometric assembly views of two adjacent segments and an individual segment, respectively, from the embodiment shown in FIG. 10. As seen in FIG. 11A, backbone 202 is seen with the lumen 221, which may be used to provide a working channel, as described above. Also seen are channel 212 defined in cable guide 210 as well as opening 214 for the cable 208 to run through. In interconnecting adjacent segments and to provide the requisite degree-of-freedom between segments, a preferable method of joining involves using the universal joint pivot 220. However, other embodiments, rather than using a universal joint pivot 220, may use a variety of joining methods, e.g., a flexible tube used to join two segments at their respective centers, a series of single degree-of-freedom joints that may be closely spaced, etc. This particular embodiment describes the use of the universal joint pivot 220. At the ends of backbone 202 adjacent to other segments, a pair of universal yoke members 224 may be formed with a pair of corresponding pin openings 226. As the universal joint pivot 220 is connected to a first pair of yoke members 224 on one segment, a corresponding pair of yoke members 224 from the adjacent segment may also be attached to the joint pivot 220.

As seen further in FIG. 11B, the universal joint pivot 220 is shown in this embodiment as a cylindrical ring having two sets of opposing receiving holes 228 for pivotally receiving corresponding yoke members 224. The receiving holes 228 are shown as being spaced apart at 90° intervals, however, in other variations, receiving holes may be spaced apart at other angles depending upon the desired degree-of-freedom and application. Also seen is an exploded assembly of spool 206 removed from motor 204 exposing drive shaft 205. With motor 204 displaced from backbone 202, the groove 230 is revealed as formed in the backbone 202. This groove 230 may be depressed in backbone 202 to preferably match the radius of the motor 204 housing not only to help locate the motor 204 adjacent to backbone 202, but also to help in reducing the overall diameter of the assembled segment. The motor 204 may be attached to the backbone 202 by various methods, e.g., adhesives, clamps, bands, mechanical fasteners, etc. A notched portion 232 may also be formed in the cable guide 210 as shown to help in further reducing segment diameter.

Prior to insertion into a patient, the endoscope 200 may be wound onto the rotating drum 184 within the rotary housing 180 of FIG. 5 for storage and during use, where it may optionally be configured to have a diagnostic check performed automatically. When the endoscope 200 is wound onto the drum 184, adjacent segments 192 will have a predetermined angle relative to one another, as determined initially by the diameter of the drum 184 and the initial configuration of the storage unit in which the endoscope 200 may be positioned. During a diagnostic check before insertion, a computer may be configured to automatically sense or measure the angles between each adjacent segments 192. If any of the adjacent segments 192 indicate a relative measured angle out of a predetermined acceptable range of angles, this may indicate a segment 192 being out of position and may indicate a potential point of problems during endoscope 200 use. Accordingly, the computer may subsequently sound an audible or visual alarm and may also place each of the segments 192 into a neutral position to automatically prevent further use or to prevent any trauma to the patient.

Figure 12:
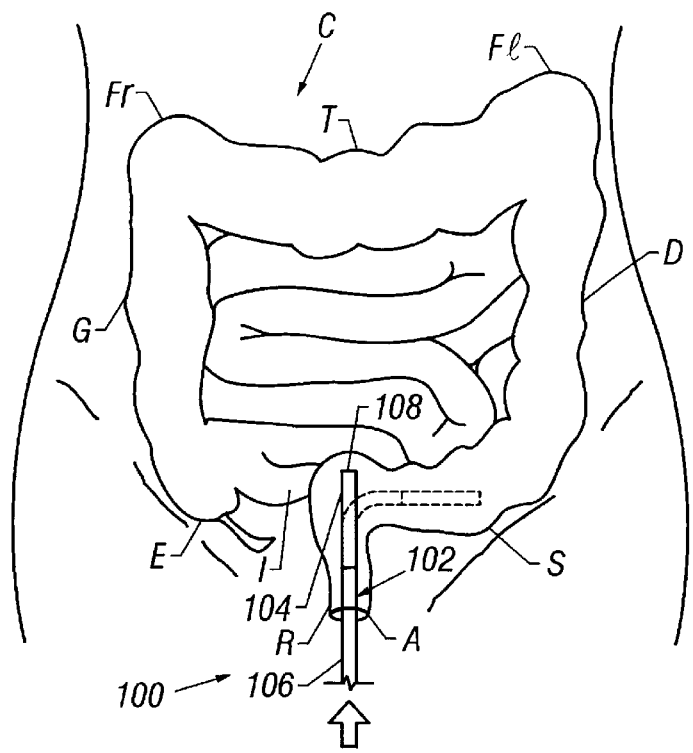
FIGS. 12–17 show the endoscope of the present invention being employed for a colonoscopic examination of a patient's colon.

FIGS. 12–17 show the endoscope 100 of the present invention being employed for a colonoscopic examination of a patient's colon. In FIG. 12, the endoscope body 102 has been lubricated and inserted into the patient's colon C through the anus A. The distal end 108 of the endoscope body 102 is advanced through the rectum R until the first turn in the colon C is reached, as observed through the ocular 124 or on a video monitor. To negotiate the turn, the selectively steerable distal portion 104 of the endoscope body 102 is manually steered toward the sigmoid colon S by the user through the steering control 122. The control signals from the steering control 122 to the selectively steerable distal portion 104 are monitored by the electronic motion controller 140. When the correct curve of the selectively steerable distal portion 104 for advancing the distal end 108 of the endoscope body 102 into the sigmoid colon S has been selected, the curve is logged into the memory of the electronic motion controller 140 as a reference. This step can be performed in a manual mode, in which the user gives a command to the electronic motion controller 140 to record the selected curve, using keyboard commands or voice commands. Alternatively, this step can be performed in an automatic mode, in which the user signals to the electronic motion controller 140 that the desired curve has been selected by advancing the endoscope body 102 distally. In this way, a three dimensional map of the colon or path may be generated and maintained for future applications.

Whether operated in manual mode or automatic mode, once the desired curve has been selected with the selectively steerable distal portion 104, the endoscope body 102 is advanced distally and the selected curve is propagated proximally along the automatically controlled proximal portion 106 of the endoscope body 102 by the electronic motion controller 140, as described above. The curve remains fixed in space while the endoscope body 102 is advanced distally through the sigmoid colon S. In a particularly tortuous colon, the selectively steerable distal portion 104 may have to be steered through multiple curves to traverse the sigmoid colon S.

Figure 13:
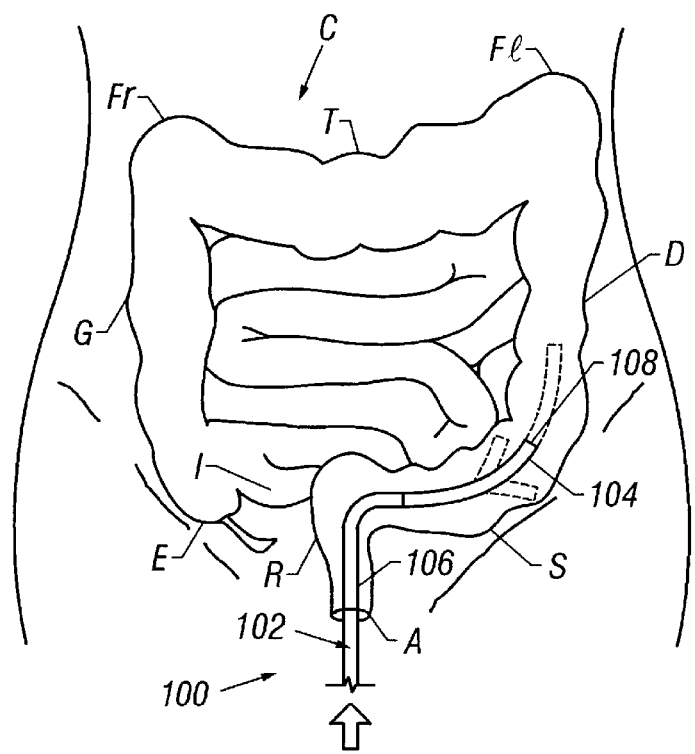
Figure 14:
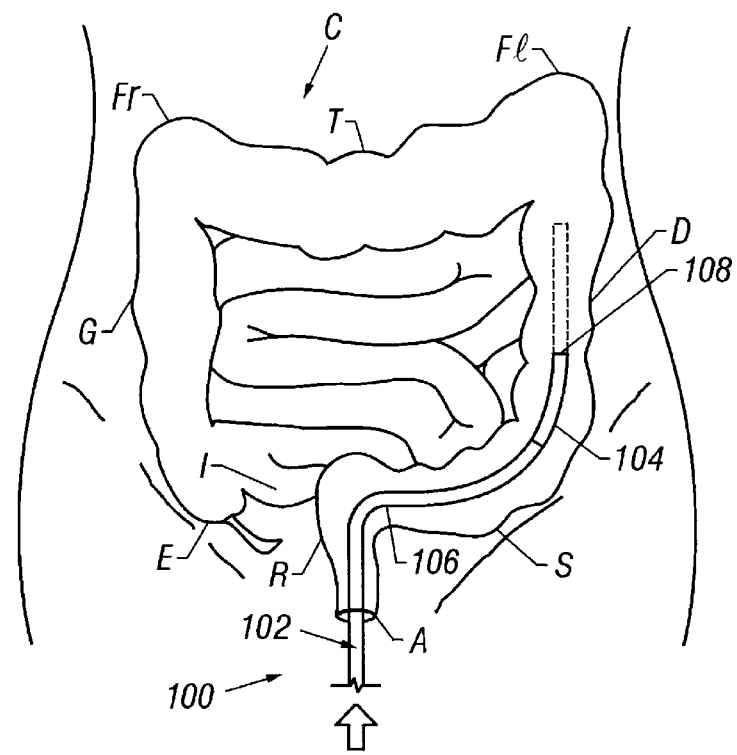

As illustrated in FIG. 13, the user may stop the endoscope 100 at any point for examination or treatment of the mucosal surface or any other features within the colon C. The selectively steerable distal portion 104 may be steered in any direction to examine the inside of the colon C. When the user has completed the examination of the sigmoid colon S, the selectively steerable distal portion 104 is steered in a superior direction toward the descending colon D. Once the desired curve has been selected with the selectively steerable distal portion 104, the endoscope body 102 is advanced distally into the descending colon D, and the second curve as well as the first curve are propagated proximally along the automatically controlled proximal portion 106 of the endoscope body 102, as shown in FIG. 14.

If, at any time, the user decides that the path taken by the endoscope body 102 needs to be revised or corrected, the endoscope 100 may be withdrawn proximally and the electronic motion controller 140 commanded to erase the previously selected curve. This can be done manually using keyboard commands or voice commands or automatically by programming the electronic motion controller 140 to go into a revise mode when the endoscope body 102 is withdrawn a certain distance. The revised or corrected curve is selected using the selectively steerable distal portion 104, and the endoscope body 102 is advanced as described before.

Figure 15:
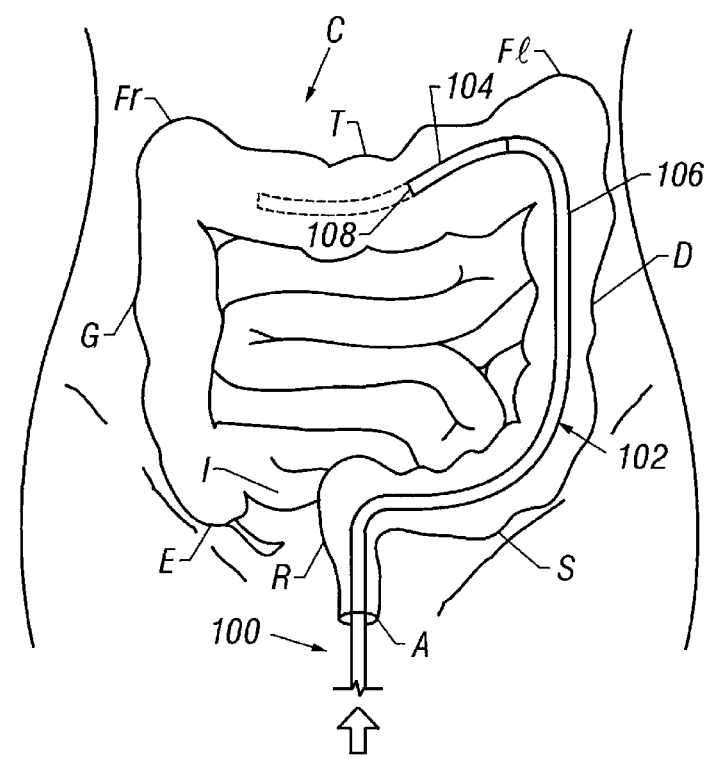
Figure 16:
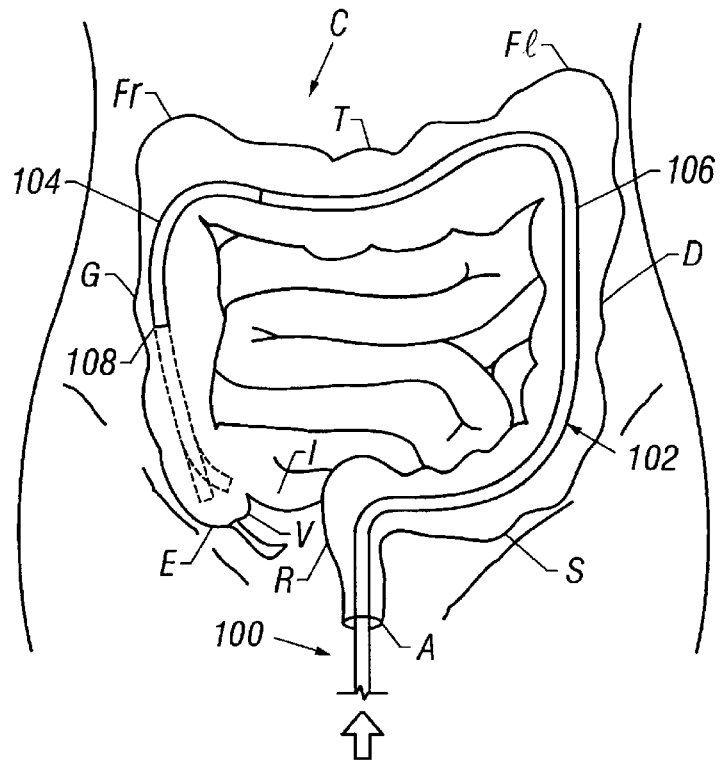

The endoscope body 102 is advanced through the descending colon D until it reaches the left (splenic) flexure $F_l$ of the colon. Here, in many cases, the endoscope body 102 must negotiate an almost 180 degree hairpin turn. As before, the desired curve is selected using the selectively steerable distal portion 104, and the endoscope body 102 is advanced distally through the transverse colon T, as shown in FIG. 15. Each of the previously selected curves is propagated proximally along the automatically controlled proximal portion 106 of the endoscope body 102. The same procedure is followed at the right (hepatic) flexure $F_r$ of the colon and the distal end 108 of the endoscope body 102 is advanced through the ascending colon G to the cecum E, as shown in FIG. 16. The cecum E, the ileocecal valve V and the terminal portion of the ileum I can be examined from this point using, the selectively steerable distal portion 104 of the endoscope body 102.

Figure 17:
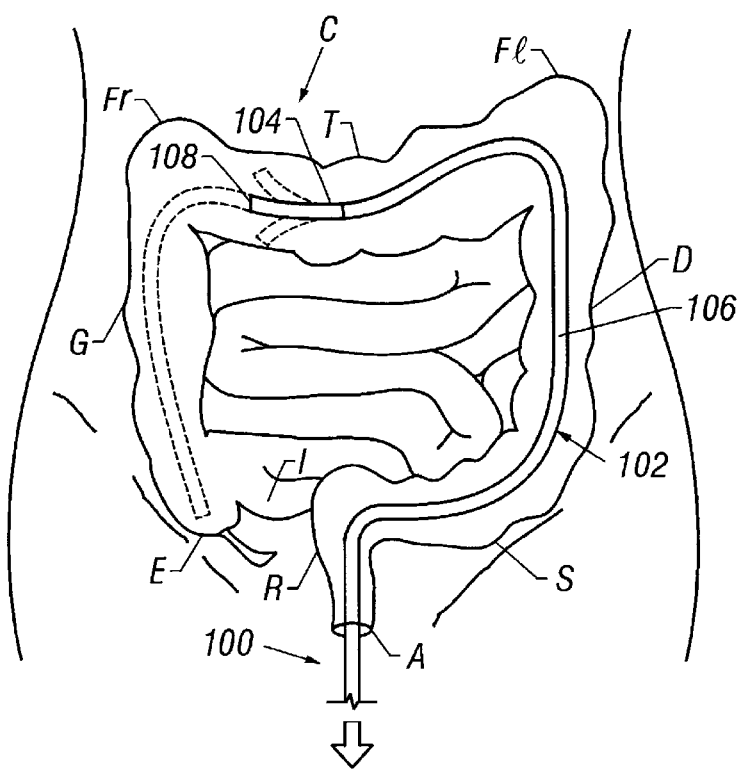

FIG. 17 shows the endoscope 100 being withdrawn through the colon C. As the endoscope 100 is withdrawn, the endoscope body 102 follows the previously selected curves by propagating the curves distally along the automatically controlled proximal portion 106, as described above. At any point, the user may stop the endoscope 100 for examination or treatment of the mucosal surface or any other features within the colon C using the selectively steerable distal portion 104 of the endoscope body 102. At any given time, the endoscope 100 may be withdrawn or back-driven by a desired distance.

In one preferred method according to the present invention, the electronic motion controller 140 includes an electronic memory in which is created a three-dimensional mathematical model of the patient's colon or other anatomy through which the endoscope body 102 is maneuvered. The three-dimensional model can be annotated by the operator to record the location of anatomical landmarks, lesions, polyps, biopsy samples and other features of interest. The three-dimensional model of the patient's anatomy can be used to facilitate reinsertion of the endoscope body 102 in subsequent procedures. In addition, the annotations can be used to quickly find the location of the features of interest. For example, the three-dimensional model can be annotated with the location where a biopsy sample was taken during an exploratory endoscopy. The site of the biopsy sample can be reliably located again in follow-up procedures to track the progress of a potential disease process and/or to perform a therapeutic procedure at the site.

In one particularly preferred variation of this method, the electronic motion controller 140 can be programmed, based on the three-dimensional model in the electronic memory, so that the endoscope body 102 will automatically assume the proper shape to follow the desired path as it is advanced through the patient's anatomy. In embodiments of the steerable endoscope 100 that are configured for automatically advancing and withdrawing the endoscope body 102, as described above in connection with FIGS. 3, 4 and 5, the endoscope body 102 can be commanded to advance automatically though the patient's anatomy to the site of a previously noted lesion or other point of interest based on the three-dimensional model in the electronic memory.

Imaging software would allow the three-dimensional model of the patient's anatomy obtained using the steerable endoscope 100 to be viewed on a computer monitor or the like. This would facilitate comparisons between the three-dimensional model and images obtained with other imaging modalities, for example fluoroscopy, radiography, ultrasonography, magnetic resonance imaging (MRI), computed tomography (CT scan), electron beam tomography or virtual colonoscopy. Conversely, images from these other imaging modalities can be used to map out an approximate path or trajectory to facilitate insertion of the endoscope body 102. In addition, images from other imaging modalities can be used to facilitate locating suspected lesions with the steerable endoscope 100. For example, images obtained using a barium-contrast radiograph of the colon can be used to map out an approximate path to facilitate insertion of the endoscope body 102 into the patient's colon. The location and depth of any suspected lesions seen on the radiograph can be noted so that the endoscope body 102 can be quickly and reliably guided to the vicinity of the lesion.

Imaging modalities that provide three-dimensional information, such as biplanar fluoroscopy, CT or MRI, can be used to program the electronic motion controller 140 so that the endoscope body 102 will automatically assume the proper shape to follow the desired path as it is advanced through the patient's anatomy. In embodiments of the steerable endoscope 100 that are configured for automatically advancing and withdrawing the endoscope body 102, the endoscope body 102 can be commanded to advance automatically though the patient's anatomy along the desired path as determined by the three-dimensional imaging information. Similarly, the endoscope body 102 can be commanded to advance automatically to the site of a suspected lesion or other point of interest noted on the images.

As described above, the axial motion transducer 150 can be made in many possible configurations, e.g., shown in FIG. 2 as a ring 152. It functions partially as a fixed point of reference or datum to produce a signal indicative of the axial position of the endoscope body 102 with respect to the fixed point of reference. The axial motion transducer 150 may use optical, electronic or mechanical methods to measure the axial position of the endoscope body 102. One preferable embodiment of the datum 234 is shown schematically in FIGS. 18–20 as an instrumented speculum which may be placed partially into the rectum of the patient or at least adjacent to the anus A of a patient. Prior to the segmented endoscopic body 238 being inserted into the anus A, it is preferably first passed through the datum channel 236 of datum 234. The datum 234 may house the electronics and mechanical assemblies necessary to measure the depth of insertion, as discussed below, and it may also provide a fixed, solid base to aid in co-locating the endoscopic body 238 adjacent to the anus A or body orifice as well as provide a base to stabilize and insert the endoscope body 238 into the orifice. The instrumented speculum may be constructed of a biocompatible material, such as injection-molded plastic, and house inexpensive electronics, as the speculum may preferably be disposable.

As the endoscopic body 238 passes through the datum channel 236, one preferable optical method of measuring the depth of insertion and axial position may involve measurement through the use of reflective infra-red sensors mounted on the datum 234. The outer surface of the endoscopic body 238 may have hatch marks or some other indicative or reflective marking placed at known intervals along the body 238. As the endoscopic body 238 is advanced or withdrawn through the anus A and the datum channel 236, an optical sensor can read or sense the hatch marks and increment or decrement the distance traveled by the endoscopic body accordingly. Thus, a sensor reading such marks may have an output that registers as a logic-level "1" or "ON" when a mark is sensed and a logic-level "0" or "OFF" when no mark is sensed. By counting or tracking the number of 1-to-0 transitions on a sensor output, the depth may be measured accordingly. Thus resolution of the depth measurement may be determined in part in this embodiment by the spacing between the hatch marks.

Figure 18:
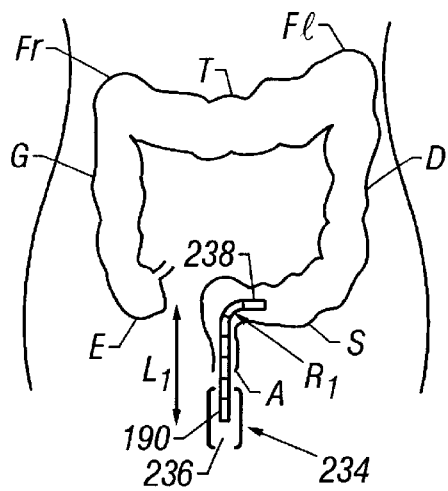
FIGS. 18–20 show an endoscope being advanced through a patient's colon while a datum measures the distance advanced into the patient.
Figure 19:
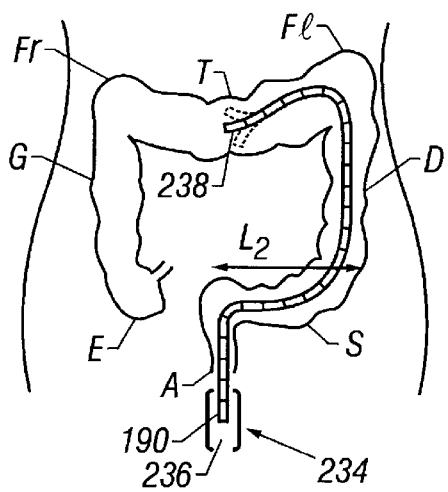
Figure 20:
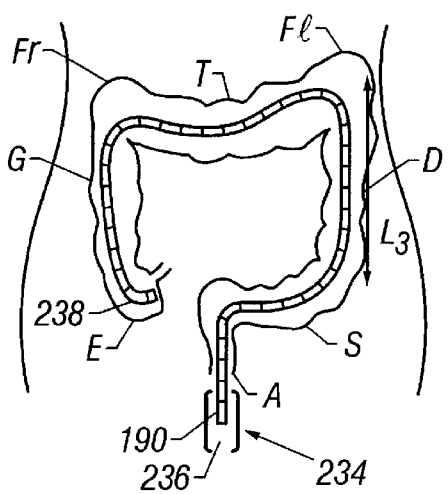

A simplified representation of how the distance may be used to advance the device may be seen in FIG. 18. The endoscopic body 238 is advanced until the distal tip reaches a depth of $L_1$, as measured from the midpoint of the datum speculum 234. At this depth, it is necessary for the user to selectively steer the tip to follow the sigmoid colon S such that the body forms a radius of curvature $R_j$. Once the position and depth of this feature has been defined by the distal tip, any proximal segment that reaches this depth of $L_1$ can be commanded to configure itself in the same manner as the distal tip segment until it has achieved the correct combination of bends to negotiate the turn. As the body 238 is further advanced, as seen in FIG. 19, it will eventually reach the second major bend at a depth of $L_1+L_2$. Accordingly, as for $L_1$, any segment that is advanced and reaches a depth of $L_1+L_2$ will likewise be commanded to execute a turn as defined by the distal tip being selectively steered when it first passed the second bend into the descending colon D. Again as the body 238 is further advanced, as shown in FIG. 20, any subsequent segment that is advanced to reach a depth of $L_1+L_2+L_3$ will be commanded to execute and negotiate the turn to follow the transverse colon T, again where the original curve has been defined by the selectively steerable distal tip.

Figure 21:
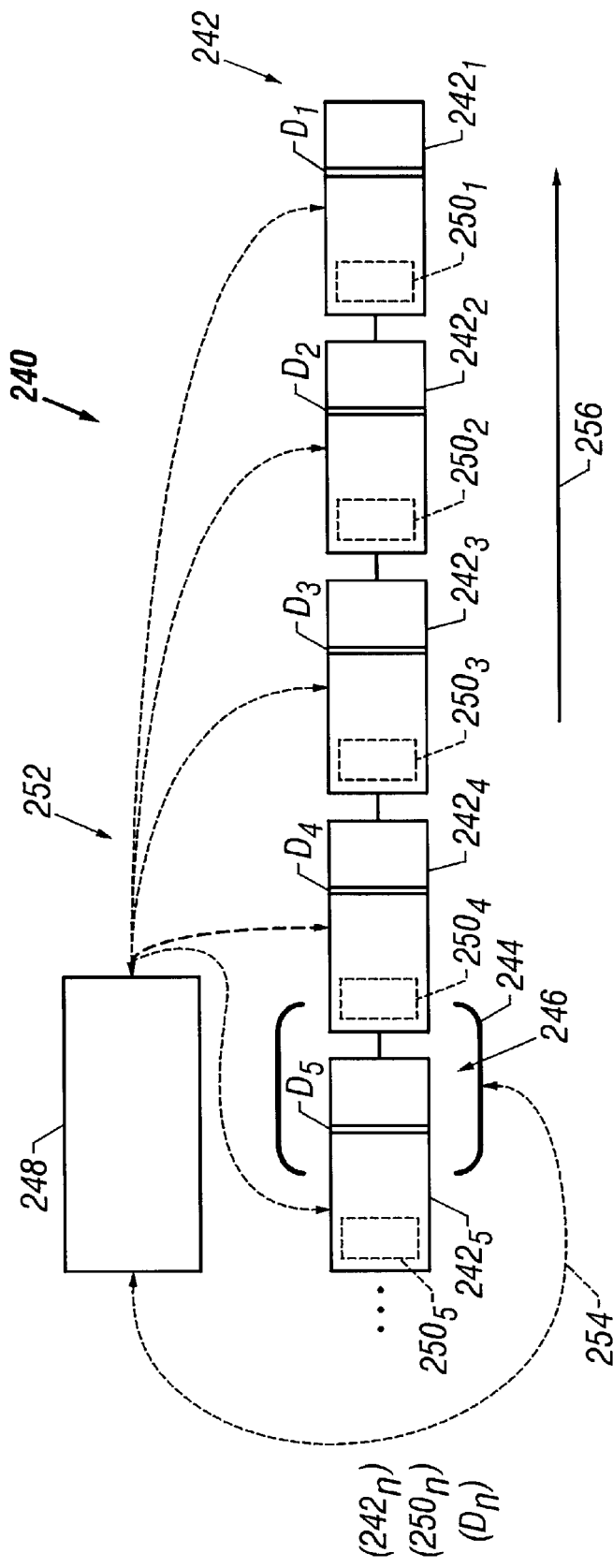
FIG. 21 shows a schematic representation of one embodiment of a control system which may be used to control and command the individual segments of a segmented endoscopic device of the type shown in FIGS. 8–11B.

FIG. 21 shows a schematic of one embodiment of a control system which may be used to control and command the individual segments of a segmented endoscopic device of the type shown in FIGS. 8–11B. As seen, a master controller 248, which preferably resides at a location away from the segmented endoscope 242, may be used to control and oversee the depth measurement as the endoscope 242 is inserted 256 into a patient. The master controller 248 may also be used to manage and communicate the actuation efforts of each of the joints and segments $242_1$ to $242_n$ by remaining in electrical communication through communications channels 252, which may include electrical wires, optical fibers, wireless transmission, etc. As also shown in this embodiment, the master controller 248 may also be in communication with datum 244 via datum communication channel 254 to measure and track the depth of insertion of the endoscope 242 as it passes through datum channel 246, as described above.

The segmented embodiment 242 may be comprised of a number of individual segments $242_1$ to $242_n$ (only segments $242_1$ to $242_5$ are shown for clarity). Each segment $242_1$ to $242_n$ preferably has its own separate controller $250_1$ to $250_n$, respectively, contained within each segment. Types of controllers used may include microcontrollers. The controllers $250_1$, to $250_n$ may serve to perform several functions, e.g., measuring the angle of each segment joint in each of the two axes $\alpha$ and $\beta$, as described above, activating the motors contained within the segments $242_1$ to $242_n$ to actuate endoscope 242 movement, and receiving and handling commands issued from the master controller 248. Having individual controllers $250_1$ to $250_n$ in each respective segment $242_1$ to $242_n$ enables each segment to manage the requirements for a given configuration locally at the controller level without oversight from the master controller 248 after a command has been issued.

Figure 22:
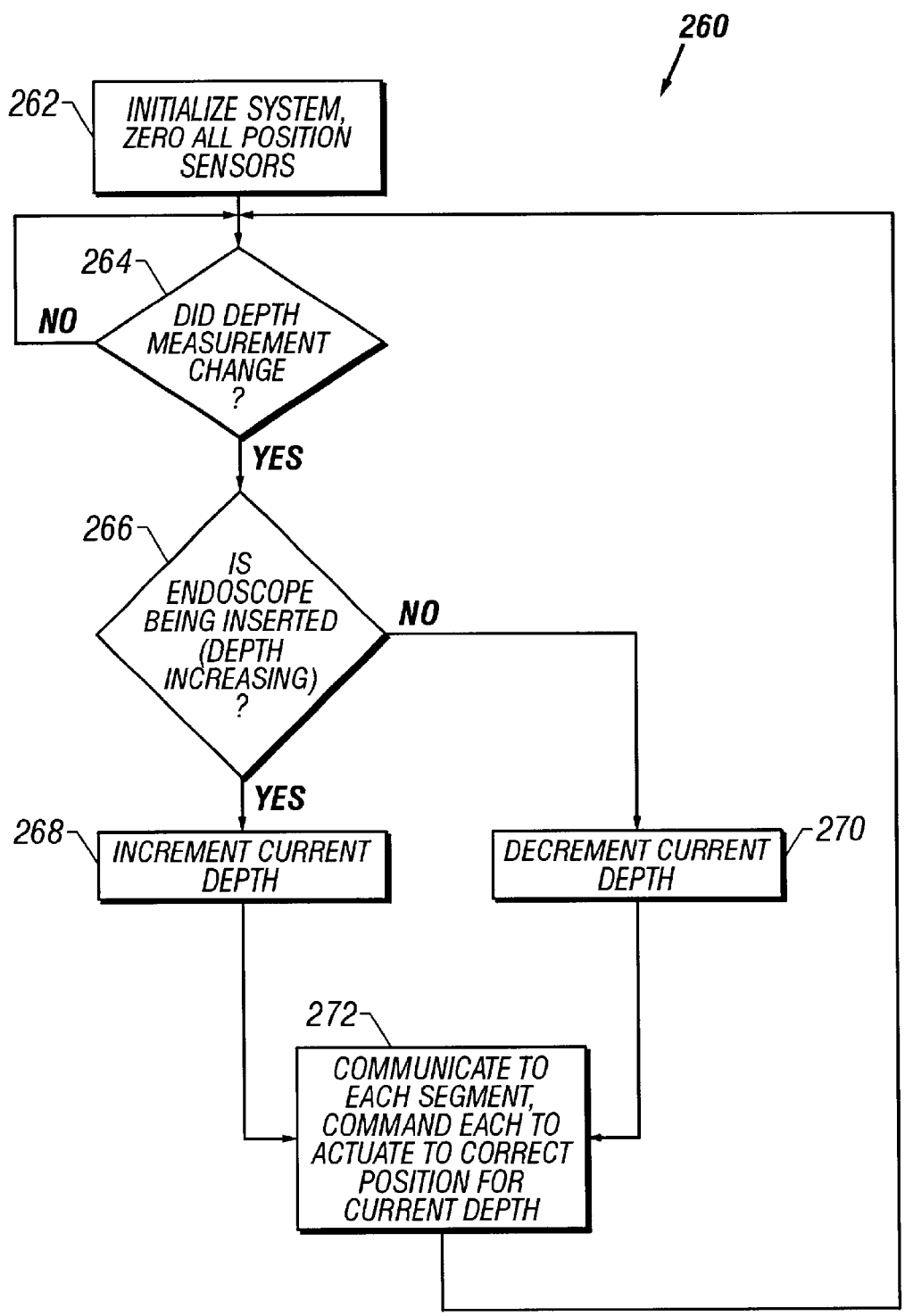
FIG. 22 shows a flow chart embodiment for the master controller algorithm which may be used to control the overall function during endoscope insertion into a patient.

Accordingly, a flow chart embodiment for the master controller algorithm 260, as shown in FIG. 22, may be used to control the overall function during insertion into a patient. During an initial step 262, the overall system (such as that shown in FIG. 21) may be initialized where all position sensors are zeroed. The master controller 248 then enters a waiting state where it continually monitors the depth measurement gathered by the datum 244 located proximally of body opening, as shown in step 264. Once movement, i.e., depth measurement, is detected by the datum 244 in step 264, the master controller 248 then determines whether the direction of motion of the endoscopic body 242 is being advanced, i.e., inserted, or withdrawn. As shown in step 266, if the endoscopic body 242 is being inserted and the depth is increasing, the current depth is incremented, as in step 268; otherwise, the current depth is decremented, as in step 270. Once the depth has been determined, the master controller 248 communicates to each segment $242_1$ to $242_n$ individually and commands each to actuate to adjust or correct its position relative to the adjacent segments for the current depth, as shown in step 272. Afterwards, the master controller 248 continues to monitor any changes in depth and the process is repeated as shown.

To maintain the orientation of each axis $\alpha$ and $\alpha$ and the positioning and the depth of each segment $242_1$ to $242_n$, a data array, or similar data structure, may be used by the master controller 248 to organize the information, as shown in the following Table 1. Depth index $D_1$ to $D_n$ is used here to denote the individual hatch marks, as seen in FIG. 21, and the distance between the hatch marks is a known value. Thus, the resolution with which the endoscope 242 can maintain its shape may depend at least in part upon the spacing between the depth indices $D_1$ to $D_n$. Moreover, the number and spacing of the indices $D_1$ to $D_n$ may be determined and set according to the specific application and necessary requirements. Additional smoothing algorithms may be used and implemented to further create gradual transitions between segments $242_1$ to $242_n$ or between discrete depth measurement indices $D_1$ to $D_n$.

TABLE 1

Data array of individual segments.

| Depth Index | Segment 1 $\alpha/\beta$ | Segment 2 $\alpha/\beta$ | ... | Segment N $\alpha/\beta$ |
|---|---|---|---|---|
| $D_1$ | $\alpha_{D1}/\beta_{D1}$ | $\alpha_{D1}/\beta_{D1}$ | ... | $\alpha_{D1}/\beta_{D1}$ |
| $D_2$ | $\alpha_{D2}/\beta_{D2}$ | $\alpha_{D2}/\beta_{D2}$ | ... | $\alpha_{D2}/\beta_{D2}$ |
| $D_3$ | $\alpha_{D3}/\beta_{D3}$ | $\alpha_{D3}/\beta_{D3}$ | ... | $\alpha_{D3}/\beta_{D3}$ |
| ... | ... | ... | ... | ... |
| $D_n$ | $\alpha_{Dn}/\beta_{Dn}$ | $\alpha_{Dn}/\beta_{Dn}$ | ... | $\alpha_{Dn}/\beta_{Dn}$ |

Figure 23:
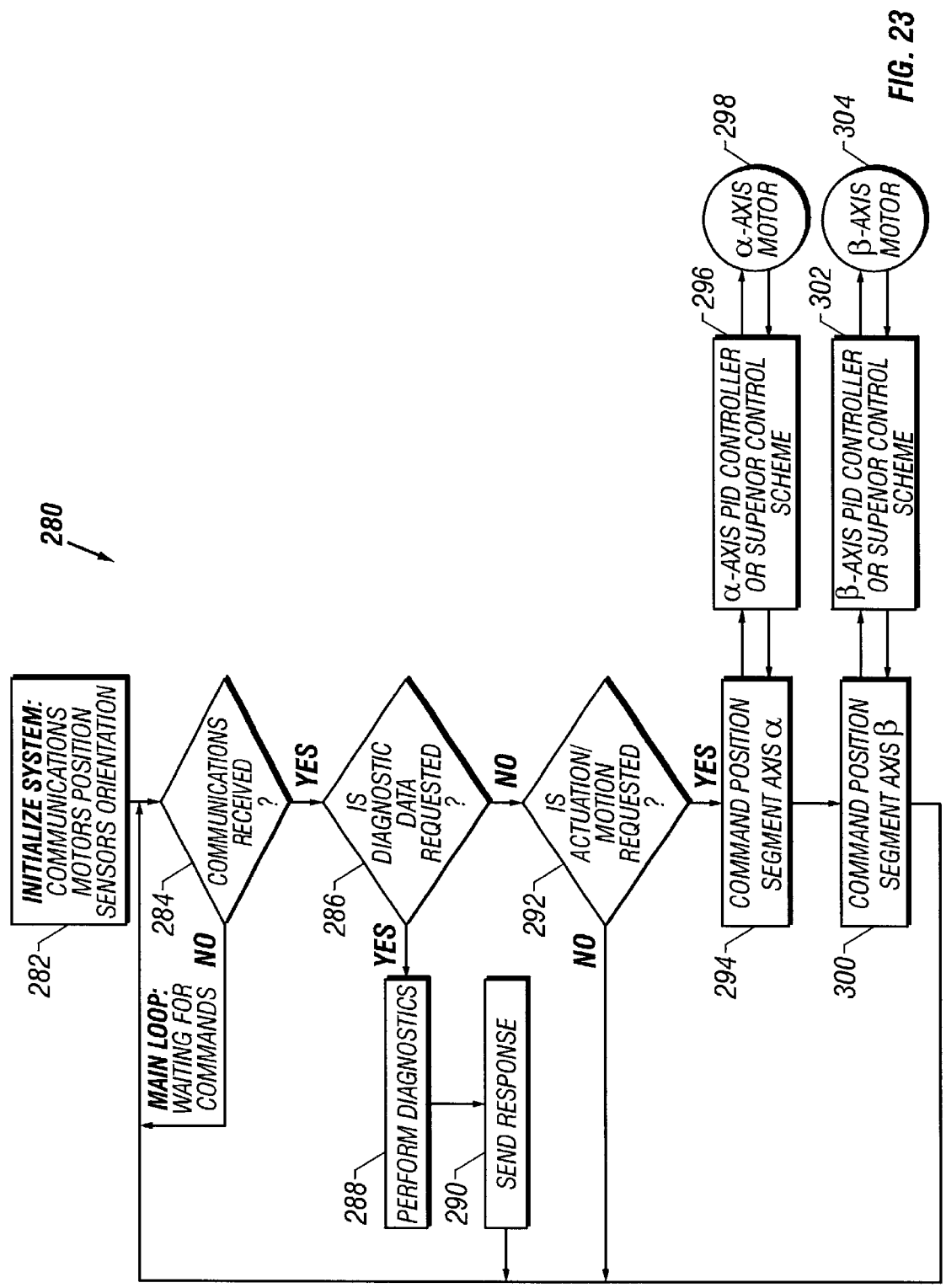
FIG. 23 shows a flowchart embodiment of the segment controller algorithm.

FIG. 23 shows a flowchart embodiment of the segment controller algorithm 280. While the master controller 248 manages the measurement of the overall depth of insertion of the endoscope 242 and determines the overall shape, it may also communicate with the individual controllers $250_1$ to $250_n$ in each segment $242_1$ to $242_n$, respectively, so that the computation task of managing the motion of the entire system is preferably distributed.

As discussed above, the individual controllers $250_1$ to $250_n$ may serve a variety of functions, including accepting commands from the master controller 248, managing communications with other controllers as necessary, measuring and controlling the position of individual segments $242_1$ to $242_n$, and performing diagnostics, error checking, etc., among other things. The algorithm to control each segment $242_1$ to $242_n$ is preferably similar for each segment; although the lead segment $242_1$ or first few segments are under the guidance of the physician to selectively control and steer so that the desired curve is set for an appropriate path to be followed.

The initial step 282 for the system preferably first occurs where all communications, actuator (or motor), position sensors, and orientation are initialized. The controllers $250_1$ to $250_n$ may then wait to receive any communications from the master controller 248 in step 284. If no communications are received, the controllers $250_1$ to $250_n$ preferably enter into a main loop while awaiting commands. When a command is received, each of the controllers $250_1$ to $250_n$ may request diagnostic data, as in step 286. If diagnostic data is requested, the appropriate diagnostics are performed in step 288 and the results are sent back to the master controller 248, as in step 290. If no diagnostic data is requested in step 286, each of the controllers $250_1$ to $250_n$ in step 292 may then determine whether actuation or motion has been requested by the master controller 248. If no actuation or motion has been requested, the relevant segment may continue to receive a command; otherwise, the relevant segment determines whether a command has been issued affecting the segment axis α, as in step 294, or segment axis β, as in step 300. If the segment axis α is to be altered, the command is sent to the α axis PID controller (or to a superior control scheme) in step 296, and the appropriate actuator is subsequently activated effecting the actuation of the segment in the α axis, as in step 298. Likewise, if the segment axis β is to be altered, either alone or in conjunction with the α axis, the command is sent to the β axis PID controller (or to a superior control scheme) in step 302, and the appropriate actuator is subsequently activated effecting the actuation of the segment in the β axis, as shown in step 304. Once the appropriate commands have been effectuated, the controllers $250_1$ to $250_n$ again enter the main loop to await any further commands.

Although the endoscope of the present invention has been described for use as a colonoscope, the endoscope can be configured for a number of other medical and industrial applications. In addition, the present invention can also be configured as a catheter, cannula, surgical instrument or introducer sheath that uses the principles of the invention for navigating through tortuous body channels.

In a variation of the method that is particularly applicable to laparoscopy or thoracoscopy procedures, the steerable endoscope 100 can be selectively maneuvered along a desired path around and between organs in a patient's body cavity. The distal end 108 of the endoscope 100 is inserted into the patient's body cavity through a natural opening, through a surgical incision or through a surgical cannula, introducer, or trocar. The selectively steerable distal portion 104 can be used to explore and examine the patient's body cavity and to select a path around and between the patient's organs. The electronic motion controller 140 can be used to control the automatically controlled proximal portion 106 of the endoscope body 102 to follow the selected path and, if necessary, to return to a desired location using the three-dimensional model in the electronic memory of the electronic motion controller 140.

Figure 24:
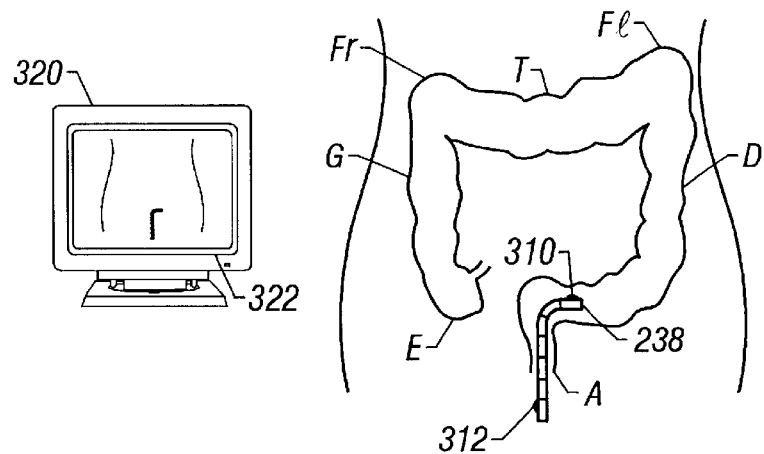
FIGS. 24–26 shows a non-contact method of measurement and tracking of an endoscope using an external navigational system such as a global positioning system.
Figure 25:
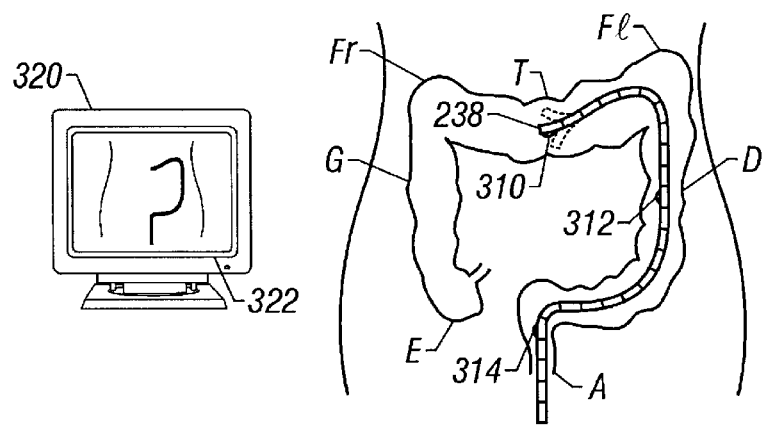
Figure 26:
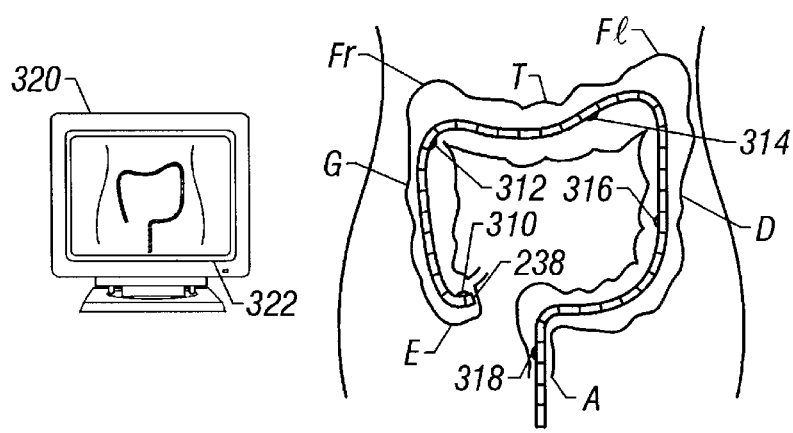

A further variation which involves a non-contact method of measurement and tracking of the steerable endoscope is seen in FIGS. 24 to 26. This variation may be used in conjunction with sensor-based systems or transponders, e.g., coils or magnetic sensors, for tracking of the endoscope via magnetic detection technology or a navigational system or device external to the patient employing a scheme similar to that used in global positioning systems (GPS). Magnetic sensors may be used, but coils are preferable because of their ability to resonate at distinct frequencies as well as their ability to have a unique "signature", which may allow for the use of several different coils to be used simultaneously. Seen in FIG. 24, the endoscopic body 238 may be inserted into a patient via the anus A. Located on the endoscope body 238 are transponders 310 to 318 which may be placed at predetermined positions such as the selectively steerable distal tip.

As the endoscope 238 is advanced through the descending D and transverse colon T, the transponders may be detected by an external navigational unit 320 which may have a display 322 showing the position of the endoscope 238 within the patient. As the endoscope 238 is further advanced within the patient, as seen in FIG. 26, the navigational unit 320 may accordingly show the corresponding movement. The use of a navigational unit 320 presents a non-contact method of navigating a device such as the endoscope 238 and may be used to measure and locate different positions within the patient relative to anatomical landmarks, such as the anus A or ileocecal valve. Furthermore, such an embodiment may be used either alone or in conjunction with the datum speculum 234 instrumentation as described above.

Use of the navigational unit 320 may also be particularly applicable to laparoscopy or thoracoscopy procedures, as described above, in spaces within the body other than the colon. For example, the endoscope 238 may also be selectively maneuvered along a desired path around and between organs in a patient's body cavity through any of the openings into the body discussed above. While being maneuvered through the body cavity, the endoscope 238 may be guided and tracked by the externally located navigational unit 320 while the endoscope's 238 location may be electronically marked and noted relative to a predetermined reference point, such as the datum, or relative to anatomical landmarks, as described above.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

We claim:

1. An apparatus for insertion into a body cavity, comprising:
    an elongate body having a proximal end and a selectively steerable distal end and defining at least one lumen therebetween, the elongate body comprising a plurality of segments interconnected via joints; and
    at least one motor attached to each of at least a majority of segments for actuating an adjacent segment and wherein each motor is independently controllable,
    wherein when the distal end assumes a selected curve, the plurality of segments are configured to propagate the selected curve along the elongate body by each motor selectively actuating the adjacent segment.

2. The apparatus of claim 1 wherein each of the segments further comprise a backbone segment defining at least one lumen therethrough, the backbone segment being configured to pivotally attach at a first or second end to the adjacent segment.

3. The apparatus of claim 1 wherein each of the joints are configured to pivotally interconnect the segments.

4. The apparatus of claim 3 wherein the joints are selected from the group consisting of universal joints, flexible tubes, a plurality of single degree-of-freedom joints, and any combinations thereof.

5. The apparatus of claim 1 wherein each of the joints are configured to have at least 2 degrees-of-freedom.

6. The apparatus of claim 1 wherein the motor comprises a type of motor selected from the group consisting of pneumatic motors, hydraulic motors, and electromechanical motors.

7. The apparatus of claim 1 wherein the motor further comprises:
   an electromechanical motor having a rotatable output shaft for actuating the adjacent segment;
   a gear reduction stage attached to the electromechanical motor; and
   a position encoder in electrical communication with the electromechanical motor for sensing an angular motion of the output shaft.

8. The apparatus of claim 7 further comprising a plurality of cables, each cable having a first end and a second end, the first end being attached to the output shaft and the second end being attached to the adjacent segment such that rotating the output shaft in a first direction actuates the adjacent segment via the cable in a first direction and rotating the output shaft in a second direction actuates the adjacent segment via the cable in a second direction.

9. The apparatus of claim 8 wherein the cable is selected from the group consisting of filaments, strands, wires, chains, and braids.

10. The apparatus of claim 8 wherein the cable is comprised of a biocompatible material selected from the group consisting of stainless steel, polymers, plastics, and Nylon.

11. The apparatus of claim 1 further comprising a microcontroller disposable in each of the segments for sensing the relative position of the adjacent segment and for selectively controlling the motor.

12. The apparatus of claim 11 wherein the microcontroller is in communication with a master controller located away from the elongate body.

13. The apparatus of claim 12 wherein the microcontroller is in electrical communication with the master controller.

14. The apparatus of claim 12 wherein the microcontroller is in optical communication with the master controller.

15. A system for inserting an apparatus into a body cavity, comprising:
   an elongate body having a proximal end and a selectively steerable distal end and defining a lumen therebetween, the elongate body comprising a plurality of segments interconnected via joints;
   at least one motor attached to each of at least a majority of segments for actuating an adjacent segment and wherein each motor is independently controllable, and wherein when the distal end assumes a selected curve, the selected curve is propagatable along the elongate body by each motor selectively actuating the adjacent segment; and
   a master controller in communication with each of the segments for selectively controlling each motor to alter the relative position of the adjacent segments when the selected curve is propagated along the elongate body.

16. The system of claim 15 further comprising a depth referencing device having a sensor for measuring a distance the elongate body is advanced or withdrawn from the body cavity.

17. The system of claim 16 wherein the sensor measures the distance via non-contact methods or contact methods.

18. The system of claim 17 wherein the sensor comprises a non-contact sensor selected from the group consisting of optical sensors, infra-red sensors, and electromagnetic sensors.

19. The system of claim 17 wherein the sensor comprises a contact sensor selected from the group consisting of axial motion transducers, rollers, and friction wheels.

20. The system of claim 15 further comprising a steering controller in communication with the steerable distal end for choosing the selected curve.

21. The system of claim 20 wherein the steering controller comprises a controller selected from the group consisting of joysticks and control wheels.

22. The system of claim 15 further comprising an imaging system for transmitting an image from the distal end to the proximal end of the elongated body.

23. The system of claim 22 wherein the imaging system comprises a fiberoptic imaging bundle extending from the distal end to the proximal end of the elongate body.

24. The system of claim 22 wherein the imaging system comprises a CCD or CMOS camera.

25. The system of claim 15 further comprising at least one illumination source on the elongate body for providing a source of light.

26. The system of claim 25 wherein the illumination source comprises at least one illumination fiber extending from the distal end to the proximal end of the elongate body.

27. The system of claim 15 further comprising a recording device in communication with the elongate body for recording images from the distal end of the elongate body.

28. The system of claim 15 wherein the elongate body is configured as an endoscope for insertion into a patient's body.

29. The system of claim 15 wherein the elongate body is configured as a colonoscope for insertion into a patient's colon.

30. A method of advancing an apparatus along a selected path, comprising:
   providing an elongate body having a proximal end and a selectively steerable distal end, the elongate body comprising a plurality of segments interconnected via joints and at least one motor attached to each of at least a majority of segments for actuating an adjacent segment and wherein each motor is independently controllable;
   selectively steering the distal end to assume a first selected curve along a desired path; and
   advancing the elongate body distally while controlling the proximal end of the instrument to assume the first selected curve of the distal end.

31. The method of claim 30 further comprising measuring a depth change of the elongate body while advancing the instrument distally.

32. The method of claim 31 further comprising incrementing a current depth by the depth change.

33. The method of claim 32 further comprising communicating to each segment to adjust a position of each segment while advancing the elongate body.

34. The method of claim 30 further comprising advancing the elongate body proximally while controlling the proximal end of the instrument to assume the first selected curve of the distal end.

35. The method of claim 34 further comprising measuring a depth change of the elongate body while advancing the instrument proximally.

36. The method of claim 35 further comprising decrementing a current depth by the depth change.

37. The method of claim 36 further comprising communicating to each segment to adjust a position of each segment while advancing the elongate body.

38. The method of claim 30 further comprising activating at least a first motor on a first segment to actuate the first segment while advancing the elongate body distally.

39. The method of claim 38 further comprising activating at least a second motor on a second segment to actuate the second segment while advancing the elongate body distally.

40. The method of claim 30 further comprising measuring an angle between each of the segments and comparing the measured angle to a predetermined range of angles prior to selectively steering the distal end.

41. The method of claim 40 further comprising indicating to a user upon an indication of the measured angle not being within the predetermined range of angles.

42. The method of claim 40 further comprising placing each of the segments into a neutral position relative to one another upon an indication of the measured angle not being within the predetermined range of angles.

43. A system for determining a location of an apparatus within a body cavity, comprising:

- an elongate body having a proximal end and a selectively steerable distal end and defining a lumen therebetween, the elongate body comprising a plurality of segments interconnected via joints;
- at least one motor attached to each of at least a majority of segments for actuating an adjacent segment and wherein each motor is independently controllable, and wherein when the distal end assumes a selected curve, the selected curve is propagatable along the elongate body by each motor selectively actuating the adjacent segment; and
- at least one transponder disposed along the body which is detectable by an external navigational detector.

44. The system of claim 43 wherein the transponder comprises a coil having a predetermined resonant frequency.

45. The system of claim 43 wherein the transponder comprises a magnet.

46. The system of claim 43 wherein the transponder is disposed at the distal end of the elongate body.

47. The system of claim 43 further comprising a plurality of additional transponders disposed along the elongate body at predetermined positions.

48. The system of claim 43 wherein the external navigational detector comprises a global positioning device for remotely determining the sensor location within the body cavity.

* * * * *